US012630799B2

(12) United States Patent
Austerjost et al.

(10) Patent No.: US 12,630,799 B2
(45) Date of Patent: May 19, 2026

(54) AUTOMATED FOAM DETECTION

(71) Applicant: Sartorius Stedim Data Analytics AB, Umeå (SE)

(72) Inventors: Jonas Austerjost, Goettingen (DE); Jens Matuszczyk, Goettingen (DE); Robert Soeldner, Goettingen (DE); Rickard Sjoegren, Umea (SE); Christoffer Edlund, Umea (SE); David James Pollard, Bohemia, NY (US)

(73) Assignee: Sartorius Stedim Data Analytics AB, Umeå (SE)

( * ) Notice: Subject to any disclaimer, the term of this patent is extended or adjusted under 35 U.S.C. 154(b) by 493 days.

(21) Appl. No.: 18/021,949

(22) PCT Filed: Aug. 13, 2021

(86) PCT No.: PCT/EP2021/072650
§ 371 (c)(1),
(2) Date: Feb. 17, 2023

(87) PCT Pub. No.: WO2022/038061
PCT Pub. Date: Feb. 24, 2022

(65) Prior Publication Data
US 2023/0357698 A1     Nov. 9, 2023

(30) Foreign Application Priority Data

Aug. 21, 2020     (EP) .................................... 20192244

(51) Int. Cl.
*C12M 1/21*          (2006.01)
*C12M 1/06*          (2006.01)
(Continued)

(52) U.S. Cl.
CPC ............ *C12M 41/02* (2013.01); *C12M 27/02* (2013.01); *C12M 41/48* (2013.01); *G06V 10/945* (2022.01); *G06V 20/693* (2022.01); *G06V 20/698* (2022.01)

(58) Field of Classification Search
CPC ...... C12M 41/02; C12M 41/48; C12M 27/02; G06V 10/945; G06V 20/693;
(Continued)

(56) References Cited

U.S. PATENT DOCUMENTS

| | | | |
|---|---|---|---|
| 8,649,605 B2 | 2/2014 | Franz et al. | |
| 2013/0039810 A1* | 2/2013 | Riechers ................ | C12M 41/02 422/82.05 |
| 2016/0152936 A1 | 6/2016 | Bargh et al. | |

FOREIGN PATENT DOCUMENTS

| | | | | |
|---|---|---|---|---|
| CN | 109671124 | * | 4/2019 | ............ G06N 3/045 |
| CN | 109671124 A | | 4/2019 | |

(Continued)

OTHER PUBLICATIONS

International Search Report and Written Opinion for International Application No. PCT/EP2021/072650 mailed Dec. 8, 2021.
(Continued)

*Primary Examiner* — Michael L Hobbs
(74) *Attorney, Agent, or Firm* — Wolf, Greenfield & Sacks, P.C.

(57)          ABSTRACT

A computer implemented method for detecting foam on the surface of a liquid medium contained in a vessel is described. The method including the steps of receiving a sample image of at least a portion of the vessel comprising the liquid-gas interface and classifying the sample image between a first class and at least one second class, associated with different amounts of foam on the surface of the liquid. The classifying is performed by a deep neural network classifier that has been trained using a plurality of training
(Continued)

images of at least a portion of a vessel comprising a liquid-gas interface. The plurality of training images may comprise at least some images that differ from each other by one or more of: the location of the liquid-gas interface on the image, the polar and/or azimuthal angle at which the liquid-gas interface is viewed on the image, and the light intensity or colour temperature of the one or more light sources that illuminated the imaged portion of the vessel when the image was acquired. Related methods for controlling a bioprocess, for providing a tool, and related systems and computer software products are also described.

20 Claims, 7 Drawing Sheets

(51) Int. Cl.
| | | |
|---|---|---|
| *C12M 1/36* | (2006.01) | |
| *G06V 10/94* | (2022.01) | |
| *G06V 20/69* | (2022.01) | |

(58) Field of Classification Search
CPC ........ G06V 20/698; G06N 3/09; G06N 3/045; G06N 3/08; G06N 3/0464; G06N 3/096
See application file for complete search history.

(56) References Cited

FOREIGN PATENT DOCUMENTS

| CN | 110310286 A | 10/2019 |
|---|---|---|
| CN | 110751606 A | 2/2020 |
| DE | 10 2010 0121 62 A1 | 9/2011 |
| EP | 3 369 478 A1 | 9/2018 |
| JP | 2010-220499 A | 10/2010 |
| JP | 2018-105690 A | 7/2018 |
| WO | WO 2010/080340 A1 | 7/2010 |
| WO | WO 2014/020327 A1 | 2/2014 |
| WO | WO 2018/044748 A1 | 3/2018 |
| WO | WO 2018/140014 A1 | 8/2018 |
| WO | WO 2020/049094 A1 | 3/2020 |
| WO | WO 2020/198518 A1 | 10/2020 |

OTHER PUBLICATIONS

Bator et al., Feature extraction for a conditioning monitoring system in a bottling process. 2018 IEEE 23rd International Conference on Emerging Technologies and Factory Automation (ETFA) Sep. 4, 2018(1): 1201-4.

Chattopadhyay et al., Grad-CAM++: Improved Visual Explanations for Deep Convolutional Networks. arXiv:1710.11063. Nov. 9, 2018. 17 pages.

Cubuk et al., RandAugment: Practical automated data augmentation with a reduced search space. arXiv:1909.13719. Nov. 14, 2019. 13 pages.

Deng et al., Imagenet: A large-scale hierarchical image database. IEEE conference on computer vision and pattern recognition. Jun. 20, 2009. 8 pages.

He et al., Deep residual learning for image recognition. Proceedings of the IEEE conference on computer vision and pattern recognition. 2016:770-8.

Huang et al., Densely connected convolutional networks. Proceedings of the IEEE conference on computer vision and pattern recognition. 2017:4700-8.

Iandola et al., SqueezeNet: AlexNet-level accuracy with 50x fewer parameters and< 0.5 MB model size. arXiv:1602.07360. Nov. 4, 2016. 13 pages.

Kingma et al., Adam: A method for stochastic optimization. arXiv:1412.6980. Dec. 22, 2014. 9 pages.

Krizhevsky et al., Imagenet classification with deep convolutional neural networks. Advances in neural information processing systems. 2012;25. 9 pages.

Selvaraju et al., Grad-CAM: Visual Explanations from Deep Networks via Gradient-based Localization. arXiv preprint arXiv:1610.02391. Dec. 3, 2019. 23 pages.

Simonyan et al., Very deep convolutional networks for large-scale image recognition. arXiv preprint arXiv:1409.1556. Dec. 23, 2014. 13 pages.

Szegedy et al., Going deeper with convolutions. Proceedings of the IEEE conference on computer vision and pattern recognition. 2015. 9 pages.

Szegedy et al., Rethinking the inception architecture for computer vision. Proceedings of the IEEE conference on computer vision and pattern recognition. 2016:2818-26.

* cited by examiner

300 — RECEIVE PLURALITY OF TRAINING IMAGES

302 — RECEIVE PLURALITY OF CLASS LABELS

CROP IMAGES

304A — RECEIVE SELECTION FROM USER

304

304B — DEFINE AND APPY MASK TO TRAINING IMAGES

306 — TRAIN CLASSIFIER

308 — DEFINE SIGNAL(S) AND EFFECTOR(S)

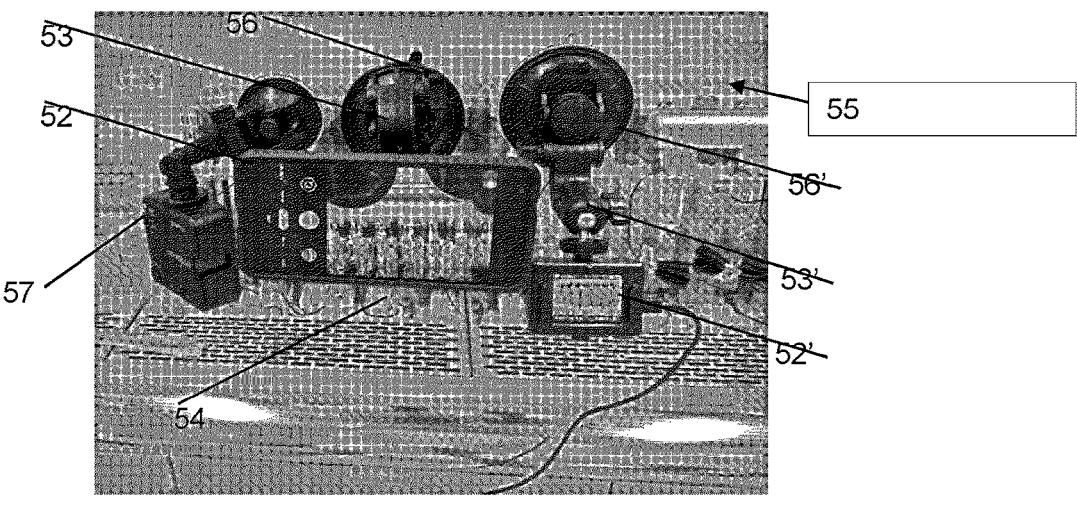
Fig. 5A
Fig. 5B
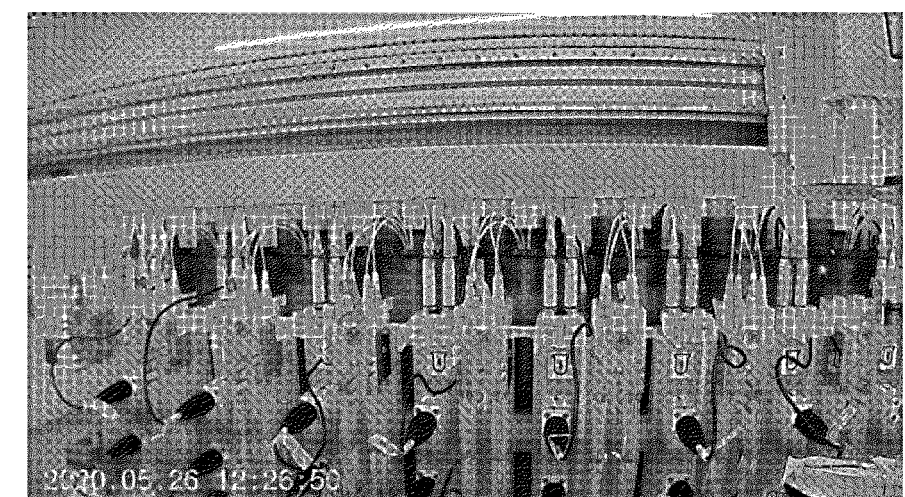
Fig. 5C
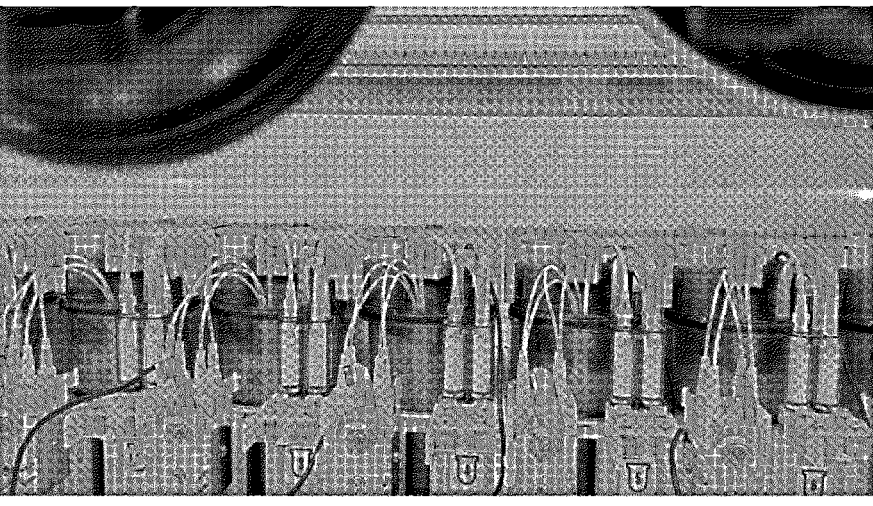

AUTOMATED FOAM DETECTION

RELATED APPLICATIONS

This Application is a National Stage filing under 35 U.S.C. 371 of International Patent Application Serial No. PCT/EP2021/072650, filed Aug. 13, 2021, which claims the benefit of European Application No. 20192244.0, filed Aug. 21, 2020, each of which is incorporated by reference in its entirety.

FIELD OF THE PRESENT DISCLOSURE

The present disclosure relates to computer implemented methods, computer programs and systems for the automated detection of foam in vessels, such as bioreactor vessels.

BACKGROUND

The emergence of surface foam is a common problem in bioprocesses such as microbial fermentation and cell culture. Foam typically appears as a result of increasing protein and cell concentrations in the culture medium in the course of the bioprocess. If left uncontrolled, foam emergence can increase to such an extent that it clogs the system filters and increases mechanical stress for the cells. Therefore, foam emergence can make it difficult to control a bioprocess, and ultimately reduce product titers obtained from the bioprocess. Antifoam agents can be added to the culture medium in order to decrease the emergence of foam. However, these agents can negatively affect the bioprocess. Indeed, high concentrations of antifoam agents can decrease oxygen transport in the culture medium (i.e. reducing the volumetric mass transfer coefficient for oxygen, commonly referred to as "kLa"), resulting in a decreased cell growth and decreased product titers. Additionally, antifoam agents have been reported to damage fermentation equipment and increase the fouling of down-streaming membranes.

Foam control in bioprocesses is commonly performed either manually, by a qualified technician triggering the addition of antifoam agents when foam is observed, or automatically by addition of antifoaming agents on a fixed time schedule. The former case is labour intensive, failure prone and suffers from reproducibility problems which may ultimately impact the quality characteristics of the product. In the latter case, the time schedule is often defined such that the addition of antifoam agent is effectively pre-emptive, i.e. antifoam agent is added in excess of what may in fact be required to control the emergence of foam, in order to prevent uncontrolled foam emergence. This leads to a sub-optimal control of the bioprocess conditions.

Foam sensors could be used to partially alleviate these problems by generating an objective criterion for addition of antifoam agents. For example, WO 2018044748 A1 describes a system for detecting the level of foam in a reactor vessel, including a light source inside the vessel and a camera that is positioned to detect changes in the intensity of the light from the light source when the level of foam in the bioreactor approaches or exceeds the level of the light source. When such a change is detected, the system can trigger the addition of an antifoaming agent to the vessel. Such a system is cumbersome to set up and lacks flexibility as it requires integration of a dedicated light and camera system with the bioreactor, and extensive and continuous calibration of the system after installation. Such a system also lacks robustness as it is calibrated for particular conditions such as a particular liquid level and light conditions.

Therefore, a need exists for a system and method for automatically detecting foam on a liquid medium contained in a vessel which is simple, flexible and robust.

SUMMARY

According to a first aspect of the disclosure, there is provided a computer-implemented method for detecting foam on the surface of a liquid medium contained in a vessel, the method including the steps of:

receiving a sample image of at least a portion of the vessel comprising the liquid-gas interface; and classifying the sample image between a first class and at least one second class, the first class and at least one second class being associated with different amounts of foam on the surface of the liquid, wherein the classifying is performed by a deep neural network classifier that has been trained using a plurality of training images of at least a portion of a vessel comprising a liquid-gas interface. The plurality of training images may comprise at least some images that differ from each other by one or more of: the location of the liquid-gas interface on the image, the polar and/or azimuthal angle at which the liquid-gas interface is viewed on the image, and the light intensity or colour temperature of the one or more light sources that illuminated the imaged portion of the vessel when the image was acquired.

The method provides an approach to detecting foam in a vessel which is flexible, highly accurate and robust. The approach does not require any specialised detection system to be integrated with the vessel, does not require specific sensors other than a standard camera, does not require any specific light source or fixed light conditions, and can be used with any vessel set up provided that at least a portion of the liquid-gas interface in the vessel can be viewed by a camera. The approach further has high accuracy in the detection of foam that is visible with the naked eye, and is highly robust to variable image acquisition conditions.

The method of the first aspect may have any one or any combination of the following optional features.

A sample image of at least a portion of the vessel comprising the liquid-gas interface may be a side view of the vessel. A side view of the vessel may advantageously enable to detect the presence of foam as well as the extent to which foam has emerged, for example by classifying the sample image between multiple second classes that are associated with different thicknesses of the foam layer on the surface of the liquid. Further, detecting the presence of foam using images showing a side view of the vessel may be performed without adaptation or integration with the vessel and associated equipment, if the vessel has at least one side-wall portion through which the liquid-gas interface is visible to the outside. Detecting the presence of foam using images showing a side view of the vessel may advantageously be performed in parallel for a plurality of vessels, using a side-view image of a plurality of vessels. As the skilled person understands, any feature described in relation to a sample image may equally apply to the training images.

Alternatively or additionally, a sample image of at least a portion of the vessel comprising the liquid-gas interface may be a top view of the vessel. A top view of the vessel may advantageously enable to detect the presence of foam in vessels that do not have a portion of side-wall through which the liquid-gas interface is visible to the outside. A top view may also be advantageous in situations where image acquisition means are preferably placed above the vessel for practical reasons, such as e.g. due to space constraints.

A sample image is preferably one that is acquired from outside the vessel. For example, a sample image may be acquired using image capture means that are located externally to the vessel. This advantageously increases the flexibility of the method since the image acquisition means can be manipulated independently of the vessel and does not require any adaptation of the vessel (provided that the liquid-gas interface or at least a portion thereof is visible from the outside of the vessel (either from the side or from the top).

The vessel shown in the sample image may be the same or different from the vessel shown in each of the plurality of training images. For example, the plurality of training images may comprise images of at least a portion of a vessel, where each training image is of the same vessel or a vessel of a similar or identical type. Further, the sample image may show a portion of the same vessel or a similar or identical type of vessel as at least one of the vessels shown in the training images. Vessels may be considered to be of a similar type when they have the same or approximately the same geometry, materials, size, or all of the above. Vessels may be considered to be of identical type when they are the same model or a corresponding model from a different make, where a corresponding model from a different make has the same geometry and size, and are made of materials of similar physical properties. For example, the vessels shown in the training images and in the sample image may all be advanced microbioreactors (such as e.g. Ambr® 250 or Ambr® 15 bioreactors from The Automation Partnership Ltd.), single use bioreactors (e.g. bag-based bioreactors such as Biostat® STR bioreactors from Sartorius Stedim Biotech GmbH), or stainless steel bioreactors (such as e.g. 5 to 2,000 I bioreactors available in the Biostat® range from Sartorius Stedim Systems GmbH). Alternatively, the vessels shown in at least some of the plurality of training images may differ from each other, and optionally also from the vessel shown in the sample image. Preferably, the vessel shown in the sample image is the same or of a similar or identical type to a vessel shown in at least some of (preferably at least 20%, 30%, 40% or 50%) the training images. As the skilled person understands, the use of training images that show a very different type of vessel from the vessel shown in the sample image may reduce the accuracy of the classification. This can be mitigated to some extent in embodiments where the sample and training images are cropped to focus on the liquid-gas interface.

The first class may be associated with the absence of foam on the surface of the liquid. The one or more second classes may be associated with the presence of foam on the surface of the liquid. The absence of foam may refer to the absence of any bubbles (such as e.g. macroscopic bubbles) on the surface of the liquid. Conversely, the presence of foam may refer to the presence of bubbles on the surface of the liquid.

Alternatively or additionally, the absence of foam may refer to the absence of clusters of bubbles on the surface of the liquid, such as e.g. the absence of a plurality of bubbles that together form a Voronoi tessellation pattern. Conversely, the presence of foam may refer to the presence of at least one cluster of bubbles on the surface of the liquid. For example, the presence of foam may refer to the presence of a plurality of bubbles that together form a Voronoi tessellation pattern.

Alternatively or additionally, the absence of foam may refer to the absence of a layer of foam on the surface of the liquid. Conversely, the presence of foam may be defined as the presence of a layer of foam on the surface of the liquid. A layer of foam may be defined as a continuous or substantially continuous area of foam that extends across the surface of a liquid in a vessel. This may be particularly advantageous when the sample image is a top view of the liquid medium in the vessel. A layer of foam may be defined as a continuous or substantially continuous area of foam that extends across at least one cross-section of the surface of a liquid in a vessel. This may be particularly advantageous when the sample image is a side view of the liquid medium in the vessel.

The one or more second classes may comprise a plurality of classes (such as e.g. a second class and at least a third class), wherein the plurality of classes are associated with the presence of different amounts of foam on the surface of the liquid. For example, a second class may be associated with the presence of a layer of foam on the surface of the liquid, and a third class may be associated with the presence of a thicker layer of foam on the surface of the liquid. The thickness of a layer of foam may be defined as the minimum or maximum thickness of the layer of foam. Alternatively or additionally, a summarised measure of thickness can be used such as e.g. the average thickness of the layer.

The one or more second classes may comprise a single class. In other words, the classifier may be a binary classifier. The present inventors have found that a binary classifier could be obtained which provided very good classification accuracy and in particular was able to reliably detect what an operator would commonly identify as a bioreactor where foam had emerged and one where foam was not present or not present in sufficient amounts to warrant an intervention. As the skilled person understands, classifiers with higher number of classes have the potential to differentiate between different amounts of foams and as such could trigger different interventions depending on the amount of foam detected. The present inventors have found that two classes were sufficient to control the emergence of foam in a conventional cell culture setting, in particular where interventions are typically binary (such as e.g. addition of a fixed dose of antifoam agent whenever foam is detected). Nevertheless, depending on the process to be regulated, higher number of classes may be advantageous and are explicitly envisaged.

The one or more second classes may comprise a plurality of classes. In other words, the classifier may be a multiclass classifier. The present inventors have found that a multiclass classifier could be obtained which provided very good classification accuracy in classifying images between 4 levels (no foam, low foam, medium foam, high foam) as assessed by an expert operator.

Images that differ from each other by the light intensity or colour temperature of the one or more light sources that illuminated the imaged portion of the vessel when the image was acquired may be characterised by different brightness levels. Brightness levels may be measured using the lightness parameter in the HSL colour model, the brightness parameter in the HSB colour model, the value parameter in the HSV colour model, the arithmetic mean of the red, green, and blue colour coordinates in the RGB colour model, or any corresponding parameter in other colour models.

Images that differ from each other by the light intensity or colour temperature of the one or more light sources that illuminated the imaged portion of the vessel when the image was acquired may have been acquired using light sources that differ in one or more of their power, colour temperature and brightness. For example, the present inventors have found that classifiers that perform exceptionally well can be obtained by training the classifier using images acquired using various combinations of lights having powers between 0.1 W and 15 W, colour temperatures between 2500K and 6500K, and brightness between 12 lux and 1000 lux. The present inventors further found that classifiers with excellent performance could be obtained by training the classifier using images acquired using various combinations of lights having powers between 0.1 W and 4.5 W, colour temperatures between 2500K and 6500K, and brightness between 12 lux and 1000 lux, even when the classifier was used to classify images exclusively acquired with a single, high power light source not present in the training data. For the avoidance of any doubt, the use of natural light (partly or exclusively) may result in images that differ from each other by the light intensity or colour temperature of the one or more light sources that illuminated the imaged portion of the vessel when the image was acquired. In other words, natural light may be considered equivalent to a plurality of light sources that differ in one or more of their power, colour temperature and brightness. Indeed, the power, colour temperature and brightness of natural light may be variable throughout acquisition of a set of training images.

Preferably, at least some of the training images differ in the amount of foam that is visible on the surface of the liquid. For example, a layer of foam at the liquid-gas interface may be visible on a first subset of the training images, and no layer of foam may be visible on a second subset of the training images.

A plurality of training images that differ from each other as indicated (i.e. by one or more of: the location of the liquid-gas interface on the image, the polar and/or azimuthal angle at which the liquid-gas interface is viewed on the image, and the light intensity or colour temperature of the one or more light sources that illuminated the imaged portion of the vessel when the image was acquired) may be a plurality of training images acquired by modifying one or more of the following parameters at least once during the image acquisition process: the volume of liquid in the vessel, the position of the image acquisition means relative to the vessel, and the light intensity (such as e.g. power or brightness) or colour temperature of the one or more light sources that illuminate the imaged portion of the vessel. Modifying the light intensity or colour temperature of the one or more light sources that illuminate the imaged portion of the vessel may comprise acquiring a plurality of training images under variable natural light (e.g. at different times of day). Modifying the light intensity or colour temperature of the one or more light sources that illuminate the imaged portion of the vessel may instead or in addition comprise acquiring a plurality of training images with one or more sources of artificial light turned on or off. Instead or in addition to this, the training images may comprise images that differ from each other by the colour of the liquid in the vessel. For example, acquiring the plurality of training images may comprise modifying the colour of the liquid in the vessel at least once during the image acquisition process (e.g. by adding a dye to the liquid or by using a liquid that has a different colour).

The vessel may be a bioreactor.

The deep neural network classifier may be a convolutional neural network (CNN). The CNN may have been pre-trained for object detection prior to training for foam detection. In such cases, training for foam detection may comprise partially re-training the pre-trained CNN. The CNN may be an 18 layers CNN. The CNN may be a CNN that has been pre-trained using a deep residual learning framework. For example, the CNN may be a CNN obtained by partially re-training ResNet18.

The deep neural network classifier may have any of the features described in relation to the ninth aspect below.

The method may further comprise sending a warning message to a user interface if the sample image is classified in the second class or a first one of a plurality of second and further classes.

Receiving a sample image of at least a portion of the vessel comprising the liquid-gas interface may comprise acquiring an image of at least a portion of the vessel comprising the liquid-gas interface.

The method may further comprise selecting an area of a received sample image comprising the liquid-gas interface, for classification.

A sample image may show at least a portion of a plurality of vessels, wherein the respective portion of the plurality of vessels comprises the liquid-gas interface. In such cases, the method may comprise selecting a plurality of areas of a received sample image, each selected area comprising the liquid-gas interface of a single respective one of the plurality of vessels, and classifying each selected area of the sample image.

Selecting an area (or a plurality of areas, as the case may be) of a received sample image may comprise applying a pre-defined mask to select an area of the received sample image. As such, the method may further comprise receiving a mask for selection of one or more areas of a sample image.

Selecting an area (or a plurality of areas, as the case may be) of a received sample image may comprise automatically defining a mask to select an area of the received sample image. For example, the method may comprise defining a mask for selection of one or more areas of a sample image by analysing the image using one or more object detection algorithms. An object detection algorithm may be, for example, a deep neural network classifier that has been trained to identify a vessel or a liquid-gas interface within a vessel, in a sample image.

The method may further comprise detecting whether the sample image differs from the plurality of training images to such an extent that no meaningful classification would be obtained. In particular, the method may comprise determining whether the sample image is an outlier with respect to the training images. This may be performed as described in WO 2020/049094. When the sample image is determined to be an outlier, the classification may not be performed, the output of the classification may not be provided to a user, and/or a warning message may be produced.

The sample image is preferably a digital image acquired using image capture means such as e.g. a digital camera. The sample image may be a colour image. For example, the sample image may be an RGB or HSV image. Without wishing to be bound by any particular theory, it is believed that colour images may be particularly advantageous as foams often appears as a different colour from the liquid medium on which they are formed, which could be used as an informative feature by the foam detection deep neural network classifier.

The image acquisition means may comprise e.g. a smart-phone.

The sample image is preferably a digital image acquired using image capture means that has distortion features similar to the distortion features in at least some of the plurality of training images. Advantageously, the sample image may have similar distortion features to the majority of training images. This can be achieved for example, by using a standard camera (e.g. a standard smartphone camera) for acquisition of both the training images (or at least some of the training images, such as e.g. a majority of the training images) and the sample image. Alternatively, this can be achieved using a camera equipped with a fish eye lens for acquisition of both the training images (or at least some of the training images, such as e.g. a majority of the training images) and the sample image.

The sample image may be a grayscale image. Without wishing to be bound by any particular theory, the inventors believe that the differences in colour frequently observed between a foam and the liquid on which it is formed is such that it is likely to be captured by a grayscale image. Black-and-white images may also be used, and are expected to be suitable for the purpose of detecting foam, albeit possibly with lower accuracy than using colour or grayscale images, since some features of the spatial organisation of a foam as opposed to a liquid are expected to be visible on black-and-white images.

At least some of the training images may have been subject to image augmentation. This may improve the robustness of the resulting classifier by increasing the size and diversity of the training data set.

According to a second aspect, there is provided a computer implemented method for controlling a bioprocess in a vessel, the method comprising:

receiving a sample image of at least a portion of the vessel comprising the liquid-gas interface;
   classifying the sample image between a first class and at least one second class, the first class and at least one second class being associated with different amounts of foam on the surface of the liquid, wherein the classifying is performed by a deep neural network classifier that has been trained using a plurality of training images of at least a portion of a vessel comprising a liquid-gas interface. The plurality of training images may comprise at least some images that differ from each other by one or more of: the location of the liquid-gas interface on the image, the polar and/or azimuthal angle at which the liquid-gas interface is viewed on the image, and the light intensity or colour temperature of the one or more light sources that illuminated the imaged portion of the vessel when the image was acquired; and
   sending a first signal to an effector device if the sample image is classified in the second class or a first one of a plurality of second and further classes.

The method according to the present aspect may have any of the features disclosed in relation to the first aspect.

The method of the present aspect may further have any one or any combination of the following optional features.

The steps of receiving a sample image and classifying the sample image may be performed by a first computing device or system (such as e.g. by a cloud computer). The step of sending a first signal to an effector device may be performed by a second computing device or system (such as e.g. a user device which is operably connected to the effector device). Therefore, the method may comprise the step of the first computing device or system communicating the classification to the second computing device or system.

An effector device may be any device coupled to the vessel and which is configured to change one or more physical or chemical conditions in the vessel. An effector device may be selected from an antifoam agent dispensing system, an agitator system (also referred to as a "stirring system"), an aeration system, a foam removal system (such as e.g. a foam suction system), and a foam destruction/ destabilisation system (e.g. a system configured to destabilise foam by means of mechanical and/or ultrasonic vibrations).

Sending a first signal to an effector device may comprise sending a signal to an antifoam agent dispensing system to cause the antifoam agent dispensing system to dispense antifoam agent in the vessel, or to cause the antifoam agent dispensing system to increase the frequency and/or amount of antifoam agent dispensed in the vessel.

Sending a first signal to an effector device may comprise sending a signal to an agitator system coupled to the vessel to cause the agitator system to decrease the agitation speed (also referred to as "stirring rate") in the vessel.

Sending a first signal to an effector device may comprise sending a signal to an aeration system coupled to the vessel to cause the aeration system to reduce the aeration rate in the vessel (e.g. reducing the volumetric flow of air or oxygen injected in the vessel).

Sending a first signal to an effector device may comprise sending a signal to a foam removal system coupled to the vessel to cause the foam removal system to remove the foam in the vessel (e.g. by activating a suction device configured to aspirate the foam, or by increasing the suction rate of such a device).

Sending a first signal to an effector device may comprise sending a signal to a foam destruction system coupled to the vessel to cause the foam destruction system to generate vibrations (e.g. ultrasonic vibrations) suitable to destabilise foam in the vessel. The vibrations may be generated in a periodic (as opposed to continuous) manner.

As the skilled person understands, sending a first signal to an effector device may in practice comprise sending a plurality of respective first signals to a plurality of effector devices. For example, a first antifoam agent dispensing signal may be sent to an antifoam agent dispensing system, and a first agitation signal may be sent to an agitator system.

The method may further comprise sending a second signal to an effector device if the sample image is classified in the first class. For example, sending a second signal to an effector device may comprise sending a signal to an antifoam agent dispensing system to cause the antifoam agent dispensing system to stop dispensing antifoam agent in the vessel or decrease the frequency and/or amount of antifoam agent dispensed in the system. Instead or in addition to this, sending a second signal to an effector device may comprise sending a signal to an agitation system coupled to the vessel to cause the agitation system to increase the agitation speed. Instead or in addition to this, sending a second signal to an effector device may comprise sending a signal to a foam removal system coupled to the vessel to cause the foam removal system to stop or decrease the removing foam in the vessel (e.g. by deactivating a suction device or decreasing the rate of suction of the device). Instead or in addition to this, sending a second signal to an effector device may comprise sending a signal to an aeration system coupled to the vessel to cause the aeration system to increase the aeration rate. Instead or in addition to this, sending a second signal to an effector device may comprise sending a signal to a foam destruction system coupled to the vessel to cause the foam destruction system to stop generating vibrations.

The method may comprise sending a third (resp. fourth, etc.) signal to an effector device if the sample image is classified in a second one (resp. third one, etc.) of a plurality of second and further classes. The first and any of the third and subsequent signal(s) (if applicable) may be dependent on the amount of foam on the surface of the liquid. In particular, a signal associated with a particular class may be different from a signal associated with another class that is associated with a different amount of foam on the surface of the liquid. For example, a signal associated with a particular class (e.g. a third signal) may be configured to cause an effector to implement a stronger antifoaming action than a signal associated with another class (e.g. a first signal) that is associated with a lower amount of foam on the surface of the liquid.

For example, sending a third signal to an effector device may comprise sending a signal to an antifoam agent dispensing system to cause the antifoam agent dispensing system to dispense antifoam in the vessel, or to cause the antifoam agent dispensing system to increase the frequency and/or amount of antifoam agent dispensed in the vessel, wherein the amounts and or frequencies are higher than those caused by the first signal. Similarly, sending a third signal to an effector device may comprise sending a signal to an agitator system coupled to the vessel to cause the agitator system to decrease the agitation speed in the vessel, wherein the decrease may be more important or to a lower agitation speed than that caused by the first signal. Instead or in addition to this, sending a third signal to an effector device may comprise sending a signal to an aeration system coupled to the vessel to cause the aeration system to decrease the aeration rate in the vessel, wherein the decrease may be more important or to a lower aeration rate than that caused by the first signal. Instead or in addition to this, sending a third signal to an effector device may comprise sending a signal to a foam removal system coupled to the vessel to cause the foam removal system to remove foam in the vessel, wherein the removal of foam may be at a higher rate (e.g. using a higher suction rate) than that caused by the first signal. Instead or in addition to this, sending a third signal to an effector device may comprise sending a signal to a foam destruction system coupled to the vessel to cause the foam removal system to generate vibrations in the vessel, wherein vibrations with different characteristics from that caused by the first signal are generated (such as e.g, wherein the vibrations are generated periodically and for intervals that are longer and/or more frequent than that caused by the first signal).

For the avoidance of any doubt, the feature of a third (resp. fourth, etc.) signal may be used alone or in combination with the feature if a second signal. The method may further comprise repeating the steps of receiving and classifying a sample image (and sending a signal to an effector device, if appropriate), for example after a predetermined period of time has elapsed since receiving the preceding image. The predetermined period of time may be fixed or may be defined depending on the results of the classification. For example, a first predetermined period of time may be used when the sample image is classified in the first class, and a second predetermined period of time may be used otherwise.

According to a third aspect, there is provided a system for detecting foam on the surface of a liquid medium contained in a vessel, the system including: at least one processor; and at least one non-transitory computer readable medium containing instructions that, when executed by the at least one processor, cause the at least one processor to perform operations comprising:

receiving a sample image of at least a portion of the vessel comprising the liquid-gas interface; and classifying the sample image between a first class and at least one second class, the first class and at least one second class being associated with different amounts of foam on the surface of the liquid, wherein the classifying is performed by a deep neural network classifier that has been trained using a plurality of training images of at least a portion of a vessel comprising a liquid-gas interface. The plurality of training images may comprise at least some images that differ from each other by one or more of: the location of the liquid-gas interface on the image, the polar and/or azimuthal angle at which the liquid-gas interface is viewed on the image, and the light intensity or colour temperature of the one or more light sources that illuminated the imaged portion of the vessel when the image was acquired.

The system according to the present aspect may be configured to implement the method of any embodiment of the first aspect. In particular, the at least one non-transitory computer readable medium may contain instructions that, when executed by the at least one processor, cause the at least one processor to perform operations comprising any of the operations described in relation to the first aspect.

According to a fourth aspect of the disclosure, there is provided a system for controlling a bioprocess, the system including:

a system for detecting foam on the surface of a liquid medium contained in a vessel according to the third aspect; and at least one effector device operably connected to the processor of the system for detecting foam on the surface of a liquid medium.

According to a fifth aspect of the disclosure, there is provided a system for controlling a bioprocess, the system including:

at least one processor; and at least one non-transitory computer readable medium containing instructions that, when executed by the at least one processor, cause the at least one processor to perform operations comprising:

receiving a sample image of at least a portion of the vessel comprising the liquid-gas interface;

classifying the sample image between a first class and at least one second class, the first class and at least one second class being associated with different amounts of foam on the surface of the liquid, wherein the classifying is performed by a deep neural network classifier that has been trained using a plurality of training images of at least a portion of a vessel comprising a liquid-gas interface, wherein the plurality of training images preferably comprise at least some images that differ from each other by one or more of: the location of the liquid-gas interface on the image, the polar and/or azimuthal angle at which the liquid-gas interface is viewed on the image, and the light intensity or colour temperature of the one or more light sources that illuminated the imaged portion of the vessel when the image was acquired; and sending a first signal to an effector device if the sample image is classified in the second class or a first one of a plurality of second and further classes.

The system according to the present aspect may be configured to implement the method of any embodiment of the second aspect. In particular, the at least one non-transitory computer readable medium may contain instructions that, when executed by the at least one processor, cause the at least one processor to perform operations comprising any of the operations described in relation to the second aspect.

According to a sixth aspect of the disclosure, there is provided a bioreactor for fermentation or cell culture having one or more bioreactor vessels and one or more systems according to the third aspect for detecting foam on the surface of a liquid medium contained in the, or each, bioreactor vessel.

According to a seventh aspect, there is provided a non-transitory computer readable medium comprising instructions that, when executed by at least one processor, cause the at least one processor to perform operations comprising:

receiving a sample image of at least a portion of a vessel comprising the liquid-gas interface; and classifying the sample image between a first class and at least one second class, the first class and at least one second class being associated with different amounts of foam on the surface of the liquid, wherein the classifying is performed by a deep neural network classifier that has been trained using a plurality of training images of at least a portion of a vessel comprising a liquid-gas interface, wherein the plurality of training images comprise at least some images that differ from each other by one or more of: the location of the liquid-gas interface on the image, the polar and/or azimuthal angle at which the liquid-gas interface is viewed on the image, and the light intensity or colour temperature of the one or more light sources that illuminated the imaged portion of the vessel when the image was acquired.

The non-transitory computer readable medium may further comprise instructions that, when executed by at least one processor, cause the at least one processor to perform operations comprising: sending a first signal to an effector device if the sample image is classified in the second class or a first one of a plurality of second and further classes.

The non-transitory computer readable medium according to the present aspect may comprise instructions that that, when executed by at least one processor, cause the at least one processor to perform operations as described in relation to the first and second aspects.

According to an eight aspect, there is provided a computer program comprising code which, when the code is executed on a computer, causes the computer to perform operations comprising:

receiving a sample image of at least a portion of the vessel comprising the liquid-gas interface; and classifying the sample image between a first class and at least one second class, the first class and at least one second class being associated with different amounts of foam on the surface of the liquid, wherein the classifying is performed by a deep neural network classifier that has been trained using a plurality of training images of at least a portion of a vessel comprising a liquid-gas interface. The plurality of training images may comprise at least some images that differ from each other by one or more of: the location of the liquid-gas interface on the image, the polar and/or azimuthal angle at which the liquid-gas interface is viewed on the image, and the light intensity or colour temperature of the one or more light sources that illuminated the imaged portion of the vessel when the image was acquired.

The computer program may comprise code which, when the code is executed on a computer, causes the computer to perform operations comprising: sending a first signal to an effector device if the sample image is classified in the second class or a first one of a plurality of second and further classes.

The computer program according to the present aspect may comprise code that, when executed by a computer, cause computer to perform operations as described in relation to the first and second aspects.

According to a ninth aspect, there is provided a computer-implemented method for providing a tool for detecting foam on the surface of a liquid medium contained in a vessel, the method comprising:

receiving:

a plurality of training images of at least a portion of a vessel comprising a liquid-gas interface, wherein the plurality of training images preferably comprise at least some images that differ from each other by one or more of: the location of the liquid-gas interface on the image, the polar and/or azimuthal angle at which the liquid-gas interface is viewed on the image, and the light intensity or colour temperature of the one or more light sources that illuminated the imaged portion of the vessel when the image was acquired; and a plurality of class labels, each associated with one of the plurality of training images, wherein the class labels are selected from a first class label and at least one second class label, and associated with different amounts of foam on the surface of the liquid;

training a deep neural network classifier to classify images between a first class and at least a second class using the plurality of training images.

The method of the present aspect may further have any one or any combination of the following optional features.

Receiving a plurality of images may comprise acquiring a plurality of images, obtaining a plurality of images from a memory, or a combination thereof. Receiving a plurality of training images may comprise acquiring a plurality of images of at least a portion of the vessel comprising a liquid-gas interface, wherein acquiring the plurality of training images comprises modifying one or more of the following parameters at least once during the image acquisition process: the volume of liquid in the vessel, the position of the image acquisition means relative to the vessel, and the light intensity (such as e.g. power or brightness) or colour temperature of the one or more light sources that illuminate the imaged portion of the vessel. Modifying the light intensity or colour temperature of the one or more light sources that illuminate the imaged portion of the vessel may comprise acquiring a plurality of training images under variable natural light. Modifying the light intensity or colour temperature of the one or more light sources that illuminate the imaged portion of the vessel may instead or in addition comprise acquiring a plurality of training images with one or more sources of artificial light turned on or off. Instead or in addition to this, the training images may comprise images that differ from each other by the colour of the liquid in the vessel. For example, acquiring the plurality of training images may comprise modifying the colour of the liquid in the vessel at least once during the image acquisition process (e.g. by adding a dye to the liquid or by using a liquid that has a different colour).

The deep neural network classifier may be a convolutional neural network (CNN). Training the deep neural network classifier may comprise obtaining a pre-trained CNN and partially retraining the CNN using the training image data.

Partially retraining the CNN may comprise fixing the parameters of one or more of the lower layers of the CNN, and determining the parameters of the remaining (higher level) layers of the CNN. In embodiments, partially retraining the CNN comprises determining the parameters of the last 5 to 10 layers, such as e.g. 8 layers, of the CNN. In embodiments, partially retraining the CNN comprises determining the parameters of the last 10 to 20% of the layers of the CNN (e.g. for a 50 layers CNN, the last 5 to 10 layers may be retrained).

The CNN may have been pre-trained using unrelated image data. For example, image databases such as ImageNet are available and can be used for the purpose of training deep neural network classifiers for image analysis.

The CNN may be an 18 layers CNN. In embodiments, the CNN is a CNN that has been pre-trained using a deep residual learning framework. In embodiments, the CNN is ResNet18.

Preferably, the plurality of training images comprises at least 50, at least 75 or at least 100 images associated with a first class label and at least 50, at least 75 or at least 100 images associated with a second class label. Where multiple second class labels are used, the plurality of training images may comprise at least 50 images associated with each of the second class labels. As the skilled person understands, the availability of a sufficient amount of training data ensures that a classifier with good accuracy can be trained. The present inventors have found that at least for a binary classifier, relatively small amounts (i.e. below 1000 images) could be used to train a highly accurate classifier. The present inventors have further confirmed that a highly accurate multiclass classifier could be trained using fewer than 3000 images (such as e.g. approx. 2000 or 2,500 images).

The plurality of training images preferably comprise images associated with each of the class labels, such that the relative proportion images associated with each of the class labels is higher than 1:10 (i.e. no class is represented more than 10 times more than any other class). For example, where the classifier is a binary classifier, the plurality of training images may comprise n images associated with the first class label, and between n/10 and n*10 images associated with the second class label.

Receiving a plurality of class labels, each associated with one of the plurality of training images, may comprise displaying a plurality of training images and prompting a user to associate a class label with each of the plurality of training images. Advantageously, this may leave it up to the user to define what amount of foam they would classify in a first class, and what amount of foam they would classify in a second or subsequent class. The user may therefore be able to parameterise the training of the classifier such that it detects problematic amounts of foam according to what they believe to be problematic in their particular use case. Prompting a user to associate a class label with each of the plurality of training images may comprise classifying the plurality of images between a plurality of classes using a previously trained deep neural network classifier, and prompting a user to select the images that have been wrongly classified.

The method may further comprise selecting an area or a plurality of areas of each training image comprising the liquid-gas interface. When a plurality of areas are selected, each may be treated as a separate image for the purpose of training the classifier. Selecting an area (or a plurality of areas, as the case may be) of each training image may comprise applying a pre-defined mask to select an area of the received sample image. As such, the method may further comprise receiving a mask for selection of one or more areas of a sample image. The mask may be user defined. As such, the method may comprise prompting the user to select one or more areas on at least one training image, and defining a mask for selection of one or more areas for subsequent training images. For example, where a plurality of training images were acquired which all show the liquid-gas interface within the same area of the training images (for example where the training images were acquired using the same or similar vessels and relative position of the vessel and camera), a single mask can be defined using input from the user and applied to all images.

Selecting an area (or a plurality of areas, as the case may be) of a received sample image may comprise automatically defining a mask to select an area of the received sample image. For example, the method may comprise defining a mask for selection of one or more areas of a sample image by analysing the image using one or more object detection algorithms. An object detection algorithm may be, for example, a deep neural network classifier that has been trained to identify a vessel or a liquid-gas interface within a vessel, in a sample image.

The method may further comprise defining a first signal to be sent to an effector device (and/or a user interface) when a sample image is classified in the second class or a first one of a plurality of second and further classes by the deep neural network classifier. Defining a first signal may comprise prompting the user to select or input a first signal and/or an effector device. As previously described, references to a first signal and effector device encompass a plurality of signals and respective effector devices.

The method may further comprise defining a second signal to be sent to an effector device (and/or a user interface) when a sample image is classified in the first class by the deep neural network classifier. Defining a second signal may comprise prompting the user to select or input a second signal and/or an effector device.

The method may further comprise defining a third signal to be sent to an effector device (and/or a user interface) when a sample image is classified in a second or further one of a plurality of second and further classes by the deep neural network classifier. Defining a third signal may comprise prompting the user to select or input a second signal and/or an effector device.

According to a tenth aspect, there is provided a system for providing a tool for detecting foam on the surface of a liquid medium contained in a vessel, the system including:

at least one processor; and at least one non-transitory computer readable medium containing instructions that, when executed by the at least one processor, cause the at least one processor to perform operations comprising:

receiving:

a plurality of training images of at least a portion of a vessel comprising a liquid-gas interface, preferably wherein the plurality of training images comprise at least some images that differ from each other by one or more of: the location of the liquid-gas interface on the image, the polar and/or azimuthal angle at which the liquid-gas interface is viewed on the image, and the light intensity or colour temperature of the one or more light sources that illuminated the imaged portion of the vessel when the image was acquired; and a plurality of class labels, each associated with one of the plurality of training images, wherein the class labels are selected from a first class label and at least one second class label, and associated with different amounts of foam on the surface of the liquid; and training a deep neural network classifier to classify images between a first class and at least a second class using the plurality of training images.

The system according to the present aspect may be configured to implement the method of any embodiment of the ninth aspect. In particular, the at least one non-transitory computer readable medium may contain instructions that, when executed by the at least one processor, cause the at least one processor to perform operations comprising any of the operations described in relation to the ninth aspect.

According to an eleventh aspect, there is provided a non-transitory computer readable medium comprising instructions that, when executed by at least one processor, cause the at least one processor to perform operations comprising:

receiving:

a plurality of training images of at least a portion of a vessel comprising a liquid-gas interface, wherein the plurality of training images preferably comprise at least some images that differ from each other by one or more of: the location of the liquid-gas interface on the image, the polar and/or azimuthal angle at which the liquid-gas interface is viewed on the image, and the light intensity or colour temperature of the one or more light sources that illuminated the imaged portion of the vessel when the image was acquired; and a plurality of class labels, each associated with one of the plurality of training images, wherein the class labels are selected from a first class label and at least one second class label, and associated with different amounts of foam on the surface of the liquid; and training a deep neural network classifier to classify images between a first class and at least a second class using the plurality of training images.

The non-transitory computer readable medium according to the present aspect may comprise instructions that that, when executed by at least one processor, cause the at least one processor to perform operations as described in relation to the ninth aspect.

According to a twelfth aspect, there is provided a computer program comprising code which, when the code is executed on a computer, causes the computer to perform operations comprising:

receiving:

a plurality of training images of at least a portion of a vessel comprising a liquid-gas interface, wherein the plurality of training images preferably comprise at least some images that differ from each other by one or more of: the location of the liquid-gas interface on the image, the polar and/or azimuthal angle at which the liquid-gas interface is viewed on the image, and the light intensity or colour temperature of the one or more light sources that illuminated the imaged portion of the vessel when the image was acquired; and a plurality of class labels, each associated with one of the plurality of training images, wherein the class labels are selected from a first class label and at least one second class label, and associated with different amounts of foam on the surface of the liquid; and training a deep neural network classifier to classify images between a first class and at least a second class using the plurality of training images.

The computer program according to the present aspect may comprise code that, when executed by a computer, cause computer to perform operations as described in relation to the ninth aspect.

BRIEF DESCRIPTION OF THE DRAWINGS

Embodiments of the present disclosure will now be described by way of example with reference to the accompanying drawings in which:

FIG. 5 shows an exemplary implementation of a system for detecting foam according to the present disclosure comprising two different cameras (A) and example images acquired using each of the cameras (B, C)

Figure 1:
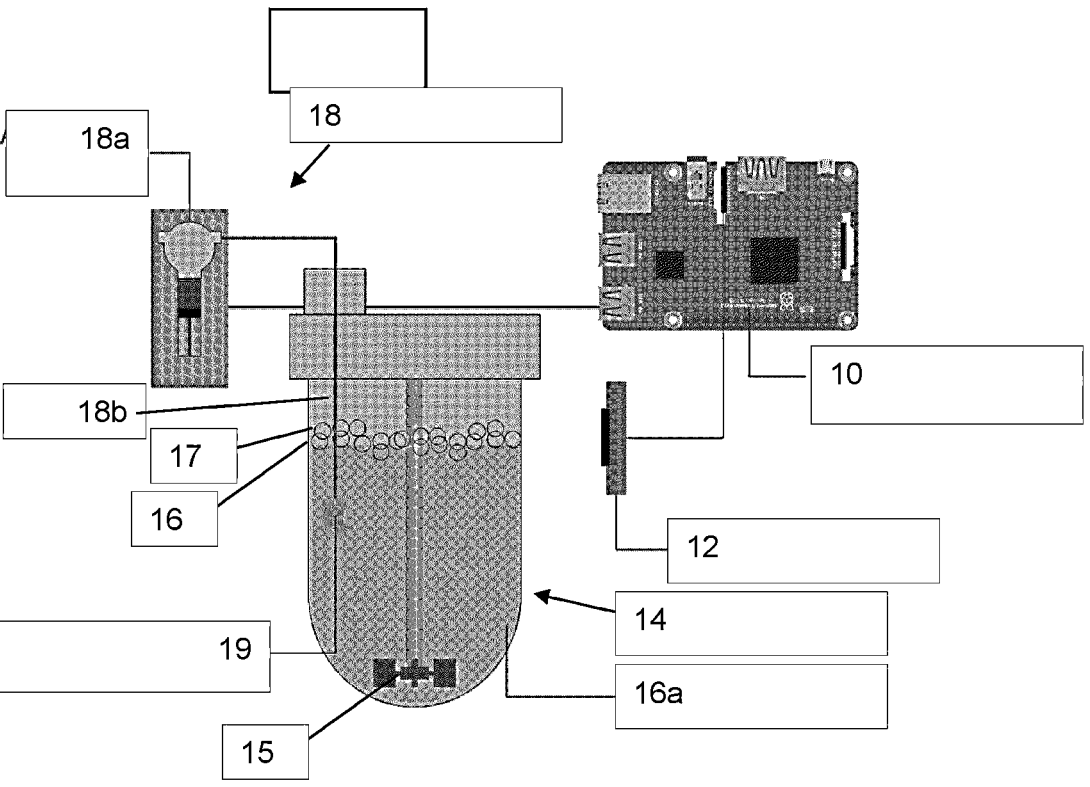
FIG. 1 shows an embodiment of a system for controlling a bioprocess according to the present disclosure.

Where the figures laid out herein illustrate embodiments of the present invention, these should not be construed as limiting to the scope of the invention. Where appropriate, like reference numerals will be used in different figures to relate to the same structural features of the illustrated embodiments.

DETAILED DESCRIPTION

Specific embodiments of the invention will be described below with reference to the Figures. As used herein, the term "bioprocess" refers to a process where biological components such as cells, organelles or bio-molecules are maintained in a liquid medium in an artificial environment such as a bioreactor. In embodiments, the bioprocess refers to a cell culture. A bioprocess typically results in a product, which can include biomass and/or one or more compounds that are produced as a result of the activity of the biological components. A bioreactor can be a single use vessel or a reusable vessel in which a liquid medium suitable for carrying out a bioprocess can be contained. Bioreactors can be configured such that at least some of the volume of the bioreactor is visible from the outside. For example, a bioreactor can comprise a section that is made from a see-through (i.e. transparent or translucent) material. The section may be limited to e.g. a window, or may encompass substantially all of the volume of the bioreactor in which the liquid medium is contained (such as e.g. where the bioreactor comprises a transparent plastic vessel such as a bag, tube or cassette). Example bioreactor systems suitable for bioprocesses are described in US 2016/0152936 and WO 2014/020327.

A "deep neural network classifier" refers to a machine learning algorithm that includes a deep neural network (an artificial neural network with multiple layers between the input and output layers) that takes as input a tensor, i.e. a data array or vector (such as e.g. a digital image), and produces as output a class prediction. A convolutional neural network is a class of deep neural networks that contains one or more hidden layers, at least some of which are convolutional layers, that together produce as output a feature vector, which is used by a fully connected layer to produce a class prediction. All of the deep neural network classifiers described herein are preferably convolutional neural network(s) (CNN). CNNs are frequently used in the field of object detection in images. Advantageously, the CNNs used may have been pre-trained on unrelated image data, such as for example from the ImageNet database (http://www.im-age-net.org). The present inventors have found an 18 layers CNN to be adequate for the present use, but alternative implementations including e.g. additional layers are envisaged. CNNs trained using a deep residual learning framework (He et al., available at https://arxiv.org/pdf/1512.03385.pdf) have been found to be particularly suitable. Other deep neural network architectures, including those that are not trained using a deep residual learning framework may be suitable and are explicitly envisaged. For example, any of the CNNs commonly referred to as AlexNet (Krizhevsky et al.), ResNet (e.g. ResNet18, ResNet 50 or ResNet101; He et al.), vgg (e.g. vgg16 or vgg19; Simonyan et al.), Squeezenet (landola et al.), Inceptionv3 (Szegedy et al., 2016), densenet (e.g. densenet201; Hunag et al.), GoogLeNet (Szegedy et al., 2015), etc.

As the skilled person would understand, references to using a deep neural network to classify image data may in practice encompass using a plurality of deep neural networks and combining the predictions of the multiple deep neural networks. Each of such a plurality of deep neural networks may have the properties described herein. Similarly, references to training a deep neural network may in fact encompass the training of multiple deep neural networks as described herein, some or all of which may subsequently be used to classify image data.

The performance of a binary classifier (or the performance of a multi-class classifier in a one-vs-remaining classes task) can be measured by quantifying the area under the receiver operating characteristic curve (AUC). As the skilled person would be aware, the receiver operating characteristic curve, or ROC curve illustrates the diagnostic ability of a binary classifier. It can be obtained by plotting the true positive rate (TPR) against the false positive rate (FPR) at various threshold settings. For example, a ROC curve can be obtained by plotting the TPR against the FPR for different values (such as e.g. every value between 0 and 1 with a step of 0.05) of a threshold applied to the predicted probability of belonging to the first severity class. In embodiments, the performance of a multiclass classifier can be measured by quantifying the Cohen's kappa coefficient and/or the percent agreement between the predicted class and the true class. Preferably, the performance of a multi-class classifier is measured by quantifying the Cohen's kappa coefficient. As the skilled person would be aware, the Cohen's kappa can be calculated as $(p_0-p_e/1-p_e)$, where $p_e$ is the relative observed agreement between the predicted class and the true class, and pe is the probability of the predicted and true class agreeing by chance (based on the amount of data that falls in each class). Alternatively, the performance of a binary classifier (or the performance of a multi-class classifier in a one-vs-remaining classes task) can be measured by quantifying the precision and/or recall of the classification achieved by the classifier on a validation dataset. The precision (also called positive predictive value) is the fraction of true positive predictions among all positive prediction (i.e. the number of true positives divided by the sum of true positives and false positives). The recall (also known as sensitivity) is the fraction of positive cases that were correctly predicted as positives (i.e. the number of true positives divided by the sum of true positives and false negatives).

FIG. 1 shows an embodiment of a system for controlling a bioprocess according to the present disclosure. The system comprises a computing device 10, which comprises a processor and computer readable memory (not shown). In the embodiment shown, the computing device is a single printed circuit board (PCB). The computing device 10 is operably connected to an image acquisition means 12. The image acquisition means can be a camera, for example an RGB camera. In embodiments, the image acquisition means can be integrated in the computing device 10. For example, the computing device may be a smartphone, tablet, personal computer or other computing device equipped with a camera. The image acquisition means 12 and the computing device 10 may be in wired connected to each other, or may be able to communicate through a wireless connection, such as e.g. through WiFi. The image acquisition 12 means is positioned relative to a vessel 14 such that it is able to capture an image of at least a portion of the vessel 14 comprising a liquid-gas interface 16. In the embodiment shown, the vessel is equipped with agitation means 15.

The computing device 10 is configured to implement a method for detecting foam 17 on the surface of the liquid medium 16a contained in the vessel 14, as described herein. In alternative embodiments, the computing device 10 is configured to communicate with a remote computing device (not shown), which is itself configured to implement a method for detecting foam 17 on the surface of the liquid medium 16a (i.e. at the liquid-gas interface 16) contained in the vessel 14, as described herein. In such cases, the remote computing device may also be configured to send the result of the method for detecting foam to the computing device. Communication between the computing device 10 and the remote computing device may be through a wired or wireless connection, and may occur over a local or public network such as e.g. over the public internet. For example, the method for detecting foam 17 on the surface of the liquid medium 16a may be performed by a cloud computing system, using images received from the computing device 10. In one example, the computing device 10 is a smartphone or tablet equipped with a camera 12, which is configured (e.g. through a native app or web app) to acquire images and either process them locally or send them to a remote computing device for processing.

The computing device 10 is operably connected with an effector device 18. The connection between the computing device 10 and the effector device 18 may be wired or wireless, and may be direct or indirect (such as e.g. through a central computer). In the embodiment shown, the effector device is an antifoaming agent dispensing system comprising a pump 18a and an injection device 18b configured to inject antifoaming agent 19 in the liquid medium 16.

Figure 2:
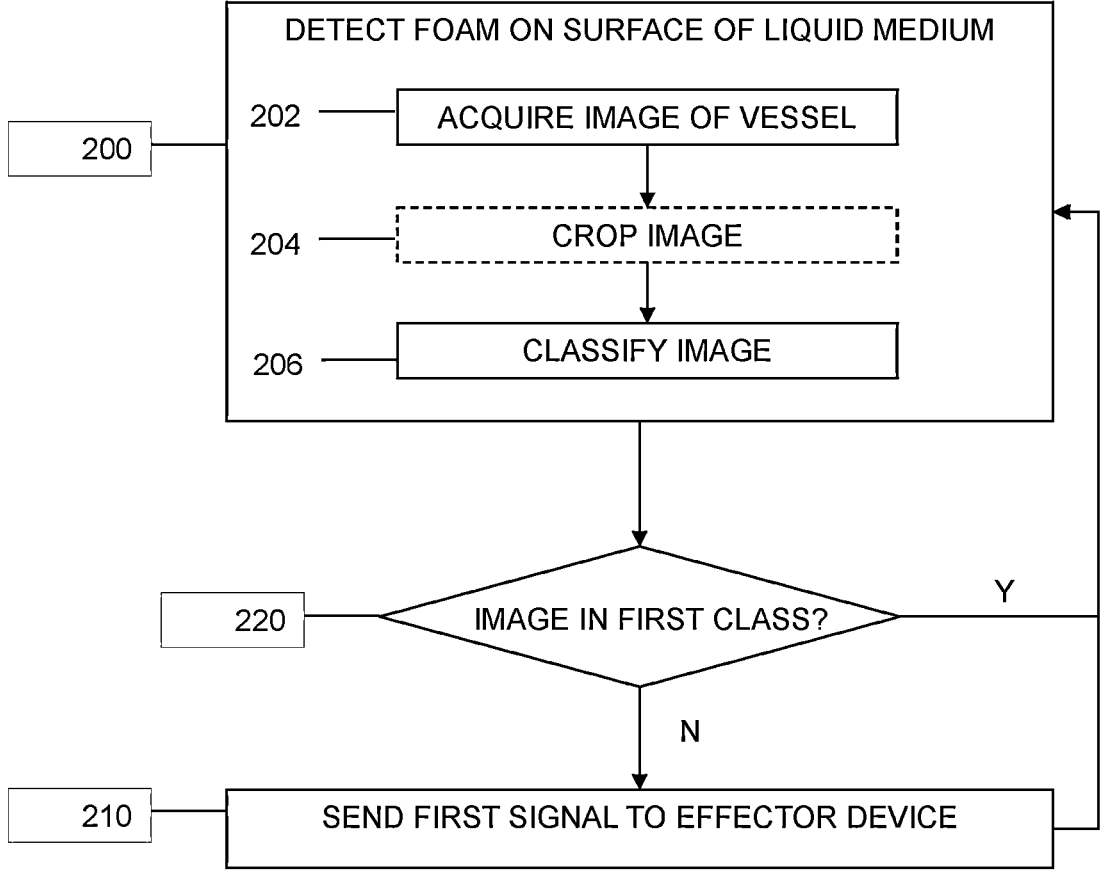
FIG. 2 is a flowchart illustrating a method of controlling a bioprocess according to embodiments of the present disclosure.

FIG. 2 is a flowchart illustrating a method of controlling a bioprocess according to embodiments of the present disclosure. The method comprises a first step 200 of detecting foam on the surface of a liquid medium contained in a vessel, and a second step 210 of controlling an effector device based on the results of the first step 200. Detecting foam on the surface of the liquid medium in a vessel comprises acquiring 202 an image of the vessel using image capture means (or receiving an image of the vessel from image capture means). The image shows at least a portion of the vessel comprising the liquid-gas interface, which is visible through a wall of the vessel or from the top of the vessel. At step 204, the image is optionally cropped 204 to select an area of the image comprising the liquid-gas interface. The image is then analysed using a deep neural network classifier at step 206. The deep neural network classifier has been trained to classify images between a first class and at least one second class, the first class and at least one second class being associated with different amounts of foam on the surface of the liquid. For example, a first class ca be a "no foam" class, and a second class can be a "foam" class. The training of the deep neural network classifier will be described in more detail in relation to FIG. 3. The method comprises assessing, at step 220, whether the deep neural network classifier has classified the image in the first class. If that is not the case, then a signal can be sent to an effector device at step 210, in order to cause the effector device to implement an action to control the emergence of foam. Instead or in addition to this, a signal can be sent to a user interface to alert the user. The process may then be repeated, for example after a pre-set time interval. If the deep neural network classifier has classified the image in the first class, the process may be repeated without a first signal being sent to an effector device. A signal may or may not be sent to a user interface in this case.

Figure 3:
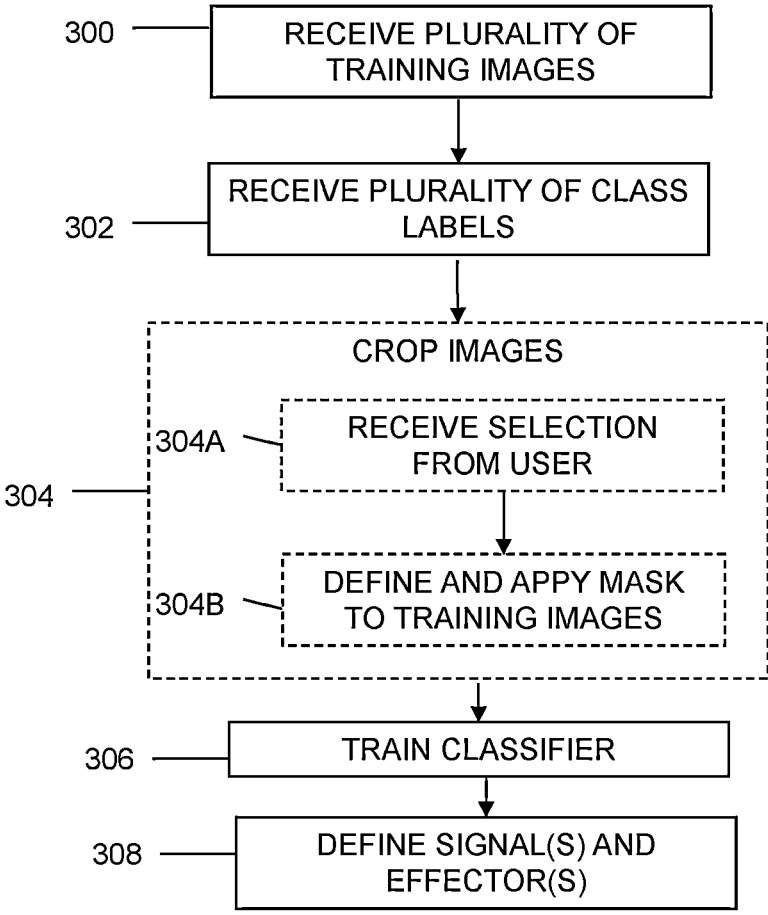
FIG. 3 is a flowchart illustrating a method of providing a tool for detecting foam according to embodiments of the present disclosure.

FIG. 3 is a flowchart illustrating a method of providing a tool for detecting foam according to embodiments of the present disclosure. The illustrated method comprises receiving 300 a plurality of training images, from a user, a memory (including a database, whether remote or local) or a combination thereof. The method further comprises receiving 302 a plurality of class labels, each associated with one of the plurality of training images, wherein the class labels are selected from a first class label and at least one second class label, and associated with different amounts of foam on the surface of the liquid. The class labels may be received from the user, or may be associated with the plurality of images in the memory from which the images were received. The training images are preferably such that the number of images associated with each of the class labels is balanced (for example by comprising no more than 10 times the amount of images in any one category), and such that each category comprises a minimum number of images (e.g. 50). This is to ensure that the classifier can be trained to detect what differentiates the class with sufficient accuracy.

The method optionally comprises cropping 304 the images, i.e. selecting an area of each mage that includes the liquid-gas interface. For example, the images may be cropped to remove uninformative sections (i.e. some or all of the background) that could otherwise confuse the classification from the classifier. The selection is preferably such that the liquid-gas interface is visible on the image within a certain tolerance in relation to the level of liquid and/or relative position of the image capture means and vessel. In other words, the selected area is preferably small enough to exclude at least some of the background and large enough to include the liquid-gas interface even in the presence of e.g. liquid level variability. It is advantageous for the cropped images to show the whole width of a vessel in which foam is to be detected. This may advantageously enable the detection of foam even if the foam does not form a continuous layer over the whole liquid-gas interface (such as e.g. where foam is particularly localized in the areas close to the walls of the vessel). Selecting an area may comprise receiving 304A a selection from a user, for example by prompting a user to select an area on a sample image, and defining 304B a mask based on this selection, which can be applied to crop other training images. As the skilled person understands, it is possible to verify whether the composition of the training data (e.g. amount of classes, number of images per class, crop area) is adequate by training the classifier using cross-validation and assessing the performance of the classifier. Overall poor performance may for example be an indication of problem with the amount of data available. Further, investigation of systematic poor performance for some images may indicate that some of the training images were not appropriately cropped.

At step 306, a deep neural network classifier is trained to classify data between the classes defined by the class labels, using the training data. This may be performed by obtaining a pre-trained CNN and partially re-training it to perform the task at hand. Further, parameters of a best performing network may be defined using cross-validation, whereby a CNN is trained on a subset of the training data and its performance validated on a further subset of the data.

The method may further comprise defining 308 signals and effectors to which these signals should be sent, depending on the output of the classification. For example, user defined actions to be performed depending on the output of the classification may be received, and signals and effectors (or user interfaces) to which these signals should be sent may be defined.

EXAMPLES

Exemplary methods of providing tools for automated foam detection, as well as exemplary methods for detecting foam, related methods, devices and systems according to the present disclosure will now be described.

Example 1—Proof-of-Principle

Figure 4:
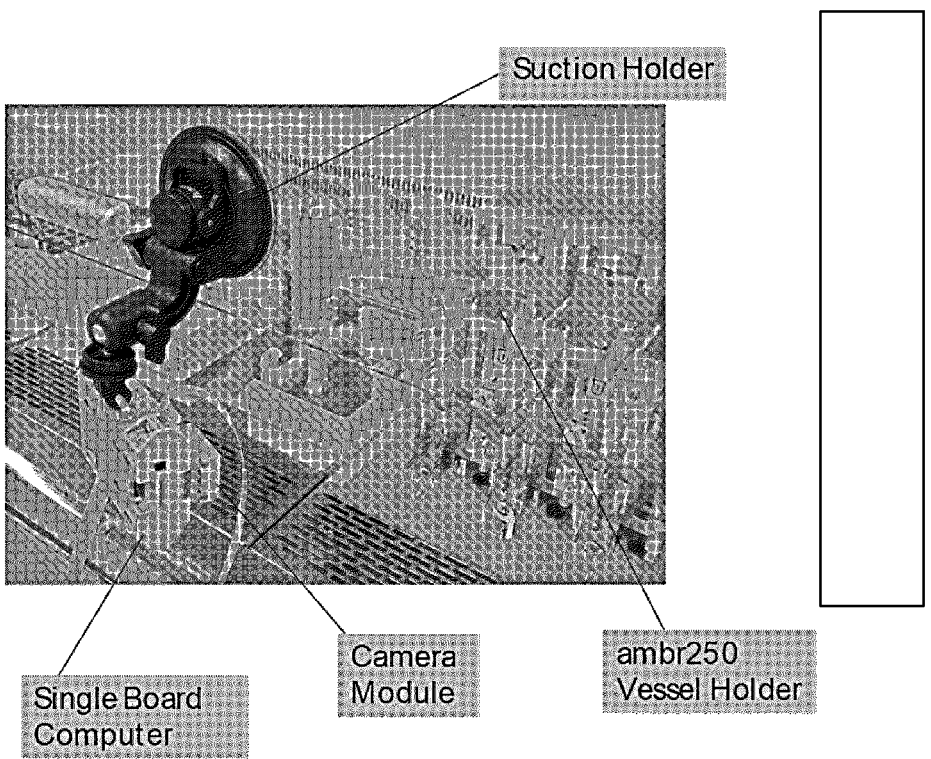
FIG. 4 shows an exemplary implementation of a system for detecting foam according to the present disclosure.

To demonstrate the feasibility of using machine vision based on deep artificial neural networks, two datasets were collected using a set up as illustrated on FIG. 4. The set up comprised a detection system comprising a computing device (in this case a single board computer) and an image acquisition means (in this case a camera module). The detection system was supported by an arm connected to a suction holder attached to the front panel of a laboratory fume hood in which a multibioreactor system was placed (in this case an Ambr® 250 vessel holder and vessels, available from Sartorius). For training, a dataset images of a single bioreaction vessel were acquired while foam was provoked by different levels of air supply and addition of a protein mixture (BSA, concentration 0.5 g\mL). All experiments were performed on an Ambre multiparallel cultivation setup. The resulting training dataset consisted of 271 images out of which 91 images where manually labelled to contain foam whereas the rest did not. In other words, the training dataset included 25.1% of images labelled as containing foam, and 74.9% of images labelled as not containing foam.

To be able to validate machine vision results, a separate dataset with images of three bioreaction vessels were collected during a second image gathering session. The second data set was acquired after removal and replacement of the suction holder holding the detection system, such that the placement and angle of the camera module differed between the training and validation data sets. For the validation dataset foam was provoked different levels of air supply and addition of a protein mixture (BSA, concentration 0.5 g\mL). The resulting validation dataset consisted of 944 images, where 109 images where manually annotated to contain foam whereas 835 did not. In other words, the validation dataset included 11.5% of images labelled as containing foam, and 88.5% of images labelled as not containing foam.

The light conditions were not controlled in either the training or validation data sets, and in particular included various combinations of intensities of artificial and natural light. Further, the level of the liquid medium in the vessels was not adjusted to be constant, and as such varied between images in both the training and validation data sets at least as a function of the amount of protein solution added to the reactor(s).

All images were colour (RGB) images, and had a resolution of 4 megapixels.

Prior to training of convolutional neural network (CNN) foam detection models, both the training and validation datasets where cropped. Of the original high-resolution images, 250×250 pixel patches centered at the bioreactor vessel liquid surface where cropped. The image resolution was chosen arbitrarily, based on availability. Without wishing to be bound by theory, the inventors believe that any resolution that is sufficient for foam to be identifiable with the naked eye in the images would be sufficient. Indeed, this ensures that the images can be labelled for training purposes, and is believed to similarly ensure that the visual features that enabled a human operator to label the images for training would also be usable by the foam detection model. It is advantageous for the cropped images to show the whole width of a vessel in which foam is to be detected. In the present setting, the 250×250 pixel patches showed the whole width of the vessels, as well as some of the surroundings of the vessel. Cropping was performed in a semi-automated way. In particular, a cropping area was defined for each bioreactor on a single image for each of the training and validation data sets, and the same area was automatically selected for cropping in all remaining images in the set. For the validation data set, as each image showed three parallel bioreactors, three separate 250×250 pixel regions were defined and used for automated cropping of the validation images. As the amount of liquid in the bioreactors was variable across the images in both the validation and training data set, the liquid level position within the cropped area was also variable.

In both datasets, a cropped image was annotated as containing foam if macroscopic foam was visible on the image at native resolution, upon manual inspection.

Then a CNN was trained to detect presence of foam using the crops from the training dataset. A Resnet18-model (He et al.) pretrained on ImageNet (Deng et al.) was trained using Adam (Kingma et al.) optimization for 10 number of epochs using a learning rate of 0.002 minimizing binary cross-entropy loss. Model building and training was implemented in Python using PyTorch (https://pytorch.org/).

The performance of the Resnet-model was then evaluated by predicting the presence of foam in the crops from the validation datasets. For the validation dataset, the model achieved 95.8% recall (fraction of the images labelled as containing foam that were correctly identified by the model as containing foam) with 100% precision (fraction of all images identified by the model as containing foam that were correctly identified). In other words, the model did not identify a single image as containing foam when the image did not in fact contain foam, and correctly identified the vast majority of images that did contain foam. This means that a system integrating this model would be able to prevent the uncontrolled emergence of foam with high reliability even in the presence of many sources of noise, and without unnecessarily implementing foam controlling operations that may negatively affect the product of the bioprocess.

Example 2—Evaluation of Robustness of a Binary and Multiclass Models

Having established that a CNN model trained to detect the presence of foam in a bioreactor could do so with high precision even in the presence of noise in the images analysed by the CNN, the inventors set out to test the robustness of the approach to a variety of conditions in the training and validation data. The inventors further demonstrated in this example the use of both a binary and multiclass classifier.

In particular, two types of models were trained:

1) binary classifiers trained to classify images between a first class (no foam), and a second class (foam); and 2) multiclass classifiers trained to classify images between a first class (no foam), and three second classes (low foam, medium foam, high foam).

As above, foam was provoked by different levels of air supply and addition of a protein mixture (BSA). All reactor systems were stirred continuously, including during image acquisition. Varied environmental parameters were applied (as described below) and videos and images were recorded. Subsequently these videos and images were manually annotated in 4 classes (no foam, low foam, mid foam, high foam) by a single expert (for consistency), and multiple models were trained based on this data. Foam was annotated as foam in presence of a uniform foam surface (not single bubbles). Furthermore the quantification (low foam, mid foam, high foam, and no foam) was done based on the subjective perception of the expert and based on the foam level reaching specific levels chosen by the expert.

The data for this example was acquired with two different cameras: an action camera and a smartphone camera. The experimental set up is shown on FIG. 5A and is similar to that of Example 1: a detection system comprising a smartphone 52, and a detection system comprising an action camera 52' were each supported by respective arms 53, 53' connected to respective suction holders 56, 56' attached to the front panel 55 of a laboratory fume hood in which a multi-parallel bioreactor system 54 was placed (in this case an Ambr® 250 vessel holder and vessels, available from The Automation Partnership Ltd.). Exemplary (raw) images obtained by the smartphone camera and the action camera are shown on FIGS. 5B and 5C, respectively. The distribution of the data between the classes and the imaging devices is shown in Table 1 below. For the binary classifier, all images labelled as low/medium/high foam were grouped in the "foam" class.

TABLE 1

| Distribution of images between classes and image acquisition means. | | | |
| --- | --- | --- | --- |
| Class | Number (%) of images (whole dataset) | Number of images (action camera) | Number of images (smartphone camera) |
| No foam | 982 (19.1%) | 17 | 965 |
| Low foam | 2183 (42.5%) | 142 | 2041 |
| Medium foam | 1542 (30.0%) | 124 | 1418 |
| High foam | 428 (8.3%) | 61 | 367 |
| Total | 5135 | 344 (6.7% of total) | 4791 (93.3% of total) |

The relative position of the two cameras and the LED spot indicated by reference numeral 57 on FIG. 5A are provided in Table 2 below.

TABLE 2

| Positions of the image acquisition means. | | |
|---|---|---|
| Smartphone | Actioncam | LED spot |
| Distance from vessel row: 40.3 cm | Distance from vessel row: 39.7 cm | Angle from reference vessel 3 |
| Distance from actioncam lens: 18.5 cm | Distance from LED spot center (lens): 26 cm | (spot center to number sticker): |
| Distance from LED spot center (lens): 7.5 cm | Lens Distance from clean bench bottom: 10 cm | 49 degree |
| Lens Distance from clean bench bottom: 17.5 cm | Angle from reference vessel 3 | |
| Angle from reference vessel 3 | (lens to number sticker): 130 degree | |
| (lens to number sticker): 65 degree | | |

Further, the impact of additional experimental variables was assessed using a Design of Experiment (DoE) approach. The following parameters were included in the DoE, each of which was varied between two values as indicated:

clean bench light (whether the built in light of the clean bench in which the multi-parallel bioreactor vessel was located was turned on): on/off;

volume (the volume of liquid in the vessel): 200 ml/240 ml;

color: whether red food dye was added to the medium (which was a standard semi-defined medium) or not.

The MODDE® software (available from Sartorius Stedim Data Analytics AB) was used to design the experiments, which were run in random order as indicated in Table 3 below.

TABLE 3

| Experimental design for image acquisition. | | | | | | | | |
|---|---|---|---|---|---|---|---|---|
| Exp No | 1 | 2 | 3 | 4 | 5 | 6 | 7 | 8 |
| Run Order | 2 | 6 | 3 | 7 | 4 | 1 | 5 | 8 |
| Volume | −1 | 1 | −1 | 1 | −1 | 1 | −1 | 1 |
| Color | −1 | −1 | 1 | 1 | −1 | −1 | 1 | 1 |
| Light | −1 | −1 | −1 | −1 | 1 | 1 | 1 | 1 |

As a further variable, the internal vessel light, and an external LED light (shown as reference numeral 57 on FIG. 5A) were randomly switched on and off. Therefore, the images used in these experiments were acquired under a variety of light conditions where for each image each of the three following light sources were either present or absent (in addition to natural light, which was not controlled):

external LED unit: Power (max.):<4.5 W; Color temperature: 5500~6500K; Brightness:>1000 lux (0.5 m);

internal vessel light: Power: 0.1 W; Color temperature: 2500-2800 K; Brightness: 12-48 lux (0.5 m);

clean bench light: Power: 15 W; Color temperature: 3000 K; Brightness: 255 lux (0.5 m).

The distribution of the data between the various experimental conditions is shown in Table 4 below.

TABLE 4

| Distribution of data between experimental conditions. | | | | | |
|---|---|---|---|---|---|
| Class | No artificial light | Clean bench light on | External LED on | Internal vessel light on | Red color medium |
| Whole data set | | | | | |
| No foam | 367 | 608 | 1 | 5 | 1 |
| Low foam | 1467 | 658 | 25 | 19 | 14 |

TABLE 4-continued

| Distribution of data between experimental conditions. | | | | | |
|---|---|---|---|---|---|
| Class | No artificial light | Clean bench light on | External LED on | Internal vessel light on | Red color medium |
| Medium | 889 | 517 | 111 | 9 | 16 |
| High foam | 114 | 222 | 72 | 10 | 10 |
| Total | 2837 | 2005 | 209 | 43 | 41 |
| Action camera data set | | | | | |
| No foam | 8 | 4 | 1 | 3 | 1 |
| Low foam | 37 | 57 | 25 | 9 | 14 |
| Medium | 50 | 30 | 24 | 4 | 16 |
| High foam | 9 | 11 | 21 | 10 | 10 |
| Total | 104 | 102 | 71 | 26 | 41 |
| Smartphone data set | | | | | |
| No foam | 359 | 604 | — | 2 | — |
| Low foam | 1430 | 601 | — | 10 | — |
| Medium | 839 | 487 | 87 | 5 | — |
| High foam | 105 | 211 | 51 | — | — |
| Total | 2733 | 1903 | 138 | 17 | — |

Three different splits of the data set were used:

1) Camera: models trained on video recorded with "smartphone" and tested on video recorded with "actioncamera";

2) Video: multiple videos were recorded with each camera, in this split the models were trained on most videos and tested on one video selected for its class balance;

3) Conditions: models were trained on video frames where the clean bench light was off (including a variety of other light conditions) and tested on frames where the "clean_bench_light_on" condition was present.

Further the effect of image augmentation was investigated by performing automated image augmentation on some of the data (but not all). Image augmentation was performed using the RandAugment technique (Cubuk et al., 2019) as implemented in the imgaug library (https://imgaug.readthedocs.io/en/latest/source/overview/collections.html), with n=0, m=6. The following augmentation policy was used: (Identity, 0., 1.0); (ShearX, 0., 0.3), #0; (ShearY, 0., 0.3), #1; (TranslateX, 0., 0.33), #2; (TranslateY, 0., 0.33), #3; (Rotate, 0, 30), #4; (AutoContrast, 0, 1), #5; (Invert, 0, 1), #6; (Equalize, 0, 1), #7; (Solarize, 0, 110), #8; (Posterize, 4, 8), #9; (Contrast, 0.1, 1.9), #10; (Color, 0.1, 1.9), #11; (Brightness, 0.1, 1.9), #12; (Sharpness, 0.1, 1.9), #13; (Cutout, 0, 0.2), #14; (SamplePairing(imgs), 0, 0.4), #15. Even where augmentation was not performed, random horizontal flips were performed.

A cloud environment was set up for the model, which allows the upload of image data to a server, which processes image material and provides the corresponding results to any client device. A client device can be any computing device, which is able to maintain an internet connection. This client device might be able to trigger actions to reduce the foam within the bioprocess (e.g. feed of antifoam agent, ultrasonic probe . . . ). Image acquisition and upload was performed with a smartphone and a client app, but other arrangements are possible. This architecture provides independence of own image processing equipment.

Model building and training was implemented in Python using PyTorch (https://pytorch.org/). All models were ResNet18 models. All models were trained using categorical cross-entropy loss (CCE) (as implemented in https://pytorch.org/docs/master/generated/torch.nn.CrossEntropyLoss.html #crossentropyloss). Models were trained for 30 epochs with a batch size of 50. Class weights were used to balance the dataset when training the binary classifier. In particular, the loss generated from the no-foam class was multiplied by a different weight from the loss generated from the foam class (which contained more training data). A weight of 1 was used for all splits for the no-foam class, and a weight of 0.4 or 0.3 was used for the foam class, respectively for the video splits (0.4) and the condition/camera splits (0.3). A random baseline was obtained for each split by Monte Carlo simulation. For each experimental split, the baseline F1 (F1=2*(precision*recall)/(precision+recall)), precision (precision=TP/(TP+FP) where TP is the number of true positives, FP is the number of false positives), recall (recall=TP/(TP+FN) where FN=number of false negatives) and accuracy (accuracy=(TP+TN)/(TP+TN+FP+FN) where TN is the number of true negatives) average scores were calculated over 10 000 random permutations. For each split and permutation, a random class label was assigned for each validation set observation, drawn from a multinomial distribution where the probabilities of belonging to each class was defined to match the current validation dataset split. The distribution of observations between the classes for each validation data set for each split is shown in Table 5 (for the binary models) and in Table 6 (for the multiclass model). The F1, precision and recall score were then calculated for the current sample compared to the ground truth validation labels. This procedure was repeated 10 000 times (leading to 10000 F1–, precision and recall scores) for the current split, and the scores were then averaged into the baseline score for that split.

TABLE 5

| Test sample distribution - binary models | | |
| --- | --- | --- |
| Split | Foam | No foam |
| Video | 477 | 195 |
| Condition | 608 | 1397 |
| Camera | 17 | 327 |

TABLE 6

| Test sample distribution - multiclass models | | | | |
| --- | --- | --- | --- | --- |
| Split | No foam | Low foam | Medium foam | High foam |
| Video | 477 | 194 | 1 | 0 |
| Condition | 608 | 658 | 517 | 222 |
| Camera | 17 | 142 | 124 | 61 |

Finally, the features of importance to the classification made by the models were investigated using Grad-CAM (Selvaraju et al., 2016) and/or Grad-CAM++ (Chattopadhyay et al., 2017). Grad-CAM uses the gradients in the last layer of a CNN with regards to a given score to calculate how much each neuron contribute to the classification. In practice this is done by the use of an average-pooling across the feature maps of the last layer, Grad-CAM++ is an extension to the Grad-CAM method which uses a weighted average focused on the positive gradients instead of the global averages. The authors of Grad-CAM++ claim to generate better heatmaps that can localize the predicted class more accurately, and with the ability to find all locations of a class instance in an image (when an object in the foreground splits the sought-after class for example). Something that Grad-CAM struggles with.

Figure 6A:
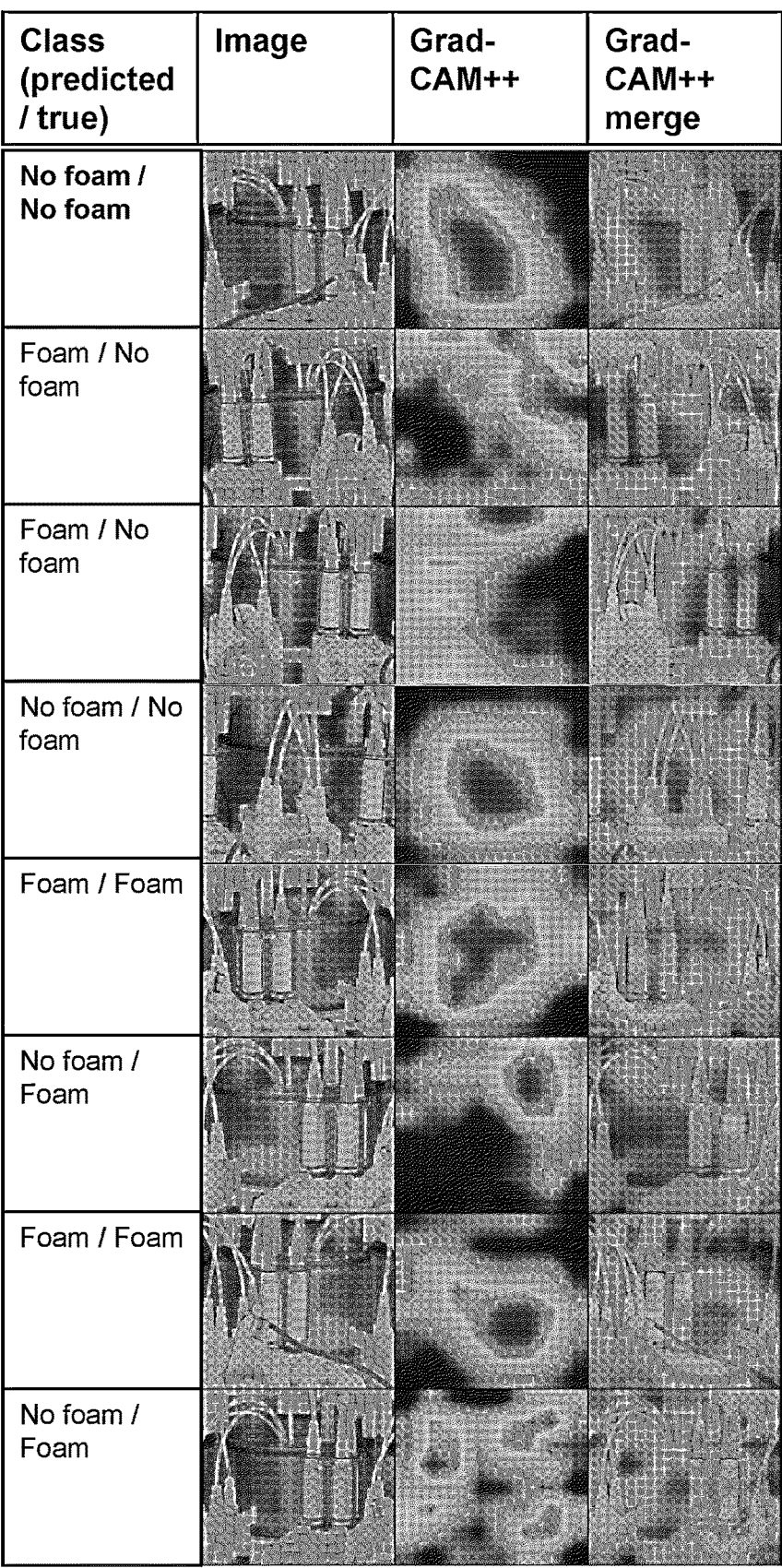
FIG. 6 shows exemplary images of at least a portion of a vessel that have been obtained using the system of FIG. 5 (column: "image"), together with the class predicted by a binary (A) and multiclass (B) foam detection model (column: "Class") and a heatmap showing the regions in each image that contributed to the classification (from a first range of colour as seen on the edge regions of the images to a second range of colours as seen in the centre of highlighted areas-column: "Grad-CAM++", column "merge" shows an overlay of the "image" and "Grad-CAM++" columns).

The results for the binary classification are shown in Table 7. The results for the multiclass classification are shown in Table 8. Example images (after cropping) and their associated Grad-CAM++ heatmaps are shown on FIG. 6 (where FIG. 6A shows examples for the binary classifier and FIG. 6B shows examples for the multiclass classifier).

The data in Tables 7 and 8 shows that all splits result in model that have good performance, and in particular significantly outperform a random baseline, apart from models that were trained exclusively on data from the smartphone camera and tested exclusively on data from the action camera (which has a fish eye lens). As can be seen on FIGS. 5C and 5B, these two cameras showed significantly different views of the vessels. As demonstrated in example 1, different angles with the same type of camera do not lead to any loss of performance. Therefore, the inventors believe that the use of the fish eye lens was likely the primary cause for the poor performance of the video split. Nevertheless, the evidence from the other splits show that using a training data set that includes images from different cameras (as is the case for the "condition" and "video" splits) results in strong performance. In other words, this indicates that where a significantly different lens is used, it is beneficial for at least some of the training data to include images obtained with a similar lens. The strong performance of the "video" splits (where the training data included images that were diverse in terms of the camera, angle, light, medium color and volume of liquid) demonstrates that a diversity of experimental conditions in the training data set results in a robust, high performance model, both in the binary and in the multiclass case. Further, the strong performance of the "condition" splits shows this benefit is maintained even when the model is trained on images with diverse relatively low light conditions and tested on images with a strong more consistent light from the clean bench light.

Figure 6B:
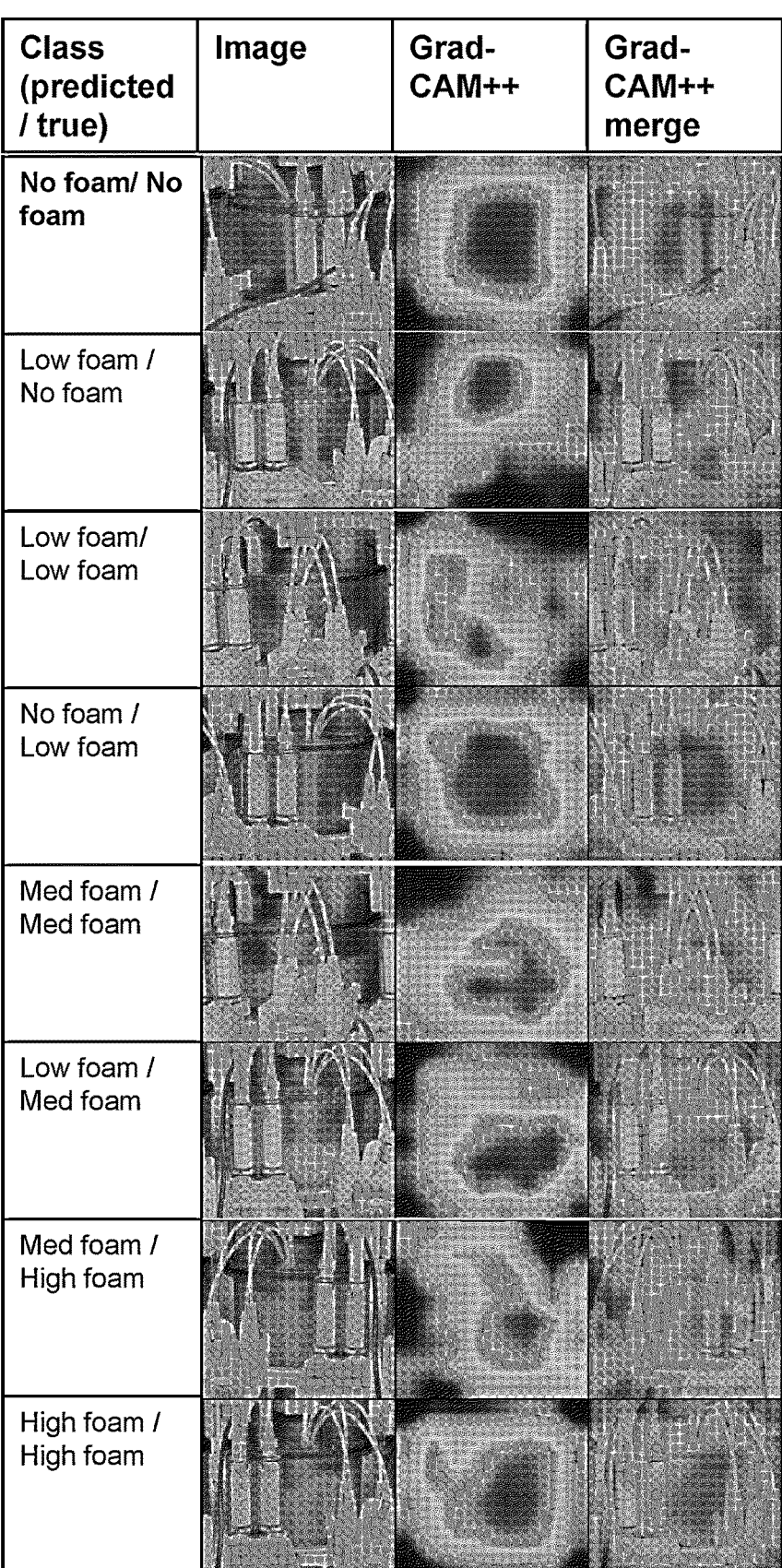

As can be seen on FIG. 6 (particularly FIG. 6B), the more foam is present, the more focus is directed to the foam area. The heatmaps on FIG. 6 show that in correctly classified images the CNN pays more attention to the liquid air interface compared to the surrounding plastic. In settings where the models are successful (which is the majority of settings, as evidenced in Tables 7 and 8), the few incorrectly classified images tend to be images with ambiguous class (i.e. edge cases where it's difficult to determine whether there is foam or not, for example because there is very little foam and/or any foam that is present is very unevenly distributed). CNNs are sensitive to edges, which is the reason the tube adapter of the vessel is highlighted as well in some images, and particularly the images that were misclassified. FIG. 6 shows examples of images that were misclassified as well as images that were correctly classified. As can be seen in Tables 7 and 8, an overwhelming majority of images were correctly classified in all splits, apart from the camera splits.

TABLE 7

| | | | | | |
|---|---|---|---|---|---|
| Experimental results - binary classification | | | | | |
| Split | Augmentation | F1 | Precision | Recall | Accuracy |
| Video | True | 0.8023 | 0.7282 | 0.8931 | 0.8958 |
| Video | False | 0.9745 | 0.9795 | 0.9695 | 0.9851 |
| Random | — | 0.3674 | 0.2904 | 0.5004 | 0.5 |
| Condition | True | 0.8945 | 0.8561 | 0.9366 | 0.8594 |
| Condition | False | 0.8099 | 0.9213 | 0.7226 | 0.6988 |
| Random | — | 0.5822 | 0.6969 | 0.5000 | 0.5 |
| Camera | True | 0.7678 | 0.6422 | 0.9545 | 0.6308 |
| Camera | False | 0.6452 | 0.4893 | 0.9467 | 0.4884 |
| Random | — | 0.6549 | 0.9506 | 0.5001 | 0.5 |

TABLE 8

| | | | | | |
|---|---|---|---|---|---|
| Experimental results - multiclass classification | | | | | |
| Split | Augmentation | F1 | Precision | Recall | Accuracy |
| Video | True | 0.5676 | 0.5544 | 0.588 | 0.8854 |
| Video | False | 0.9891 | 0.9907 | 0.9877 | 0.9866 |
| Random | — | 0.1602 | 0.2502 | 0.1869 | 0.25 |
| Condition | True | 0.5456 | 0.5768 | 0.5764 | 0.6828 |
| Condition | False | 0.3720 | 0.3825 | 0.4254 | 0.4584 |
| Random | — | 0.2413 | 0.2501 | 0.2501 | 0.25 |
| Camera | True | 0.1905 | 0.2703 | 0.3001 | 0.2878 |
| Camera | False | 0.2699 | 0.2997 | 0.3057 | 0.3517 |
| Random | — | 0.2237 | 0.2500 | 0.2500 | 0.25 |

The evidence in these examples demonstrate that a model trained as described herein is robust in terms of varied lighting, volume and color conditions and able to quantify foam in distinct levels.

REFERENCES

Deng, J., et al. "ImageNet: A Large-Scale Hierarchical Image Database." CVPR09, 2009. He, Kaiming, et al. "Deep Residual Learning for Image Recognition." *Proceedings of the IEEE Conference on Computer Vision and Pattern Recognition,* 2016, pp. 770-778.

Kingma, Diederik P., and Jimmy Ba. "Adam: A method for stochastic optimization." *arXiv preprint arXiv:* 1412.6980 (2014).

landola, Forrest N., Song Han, Matthew W. Moskewicz, Khalid Ashraf, William J. Dally, and Kurt Keutzer. "SqueezeNet: AlexNet-level accuracy with 50× fewer parameters and <0.5 MB model size." Preprint, submitted Nov. 4, 2016. https://arxiv.org/abs/1602.07360.

Szegedy, Christian, Wei Liu, Yangqing Jia, Pierre Sermanet, Scott Reed, Dragomir Anguelov, Dumitru Erhan, Vincent Vanhoucke, and Andrew Rabinovich. "Going deeper with convolutions." In Proceedings of the IEEE conference on computer vision and pattern recognition, pp. 1-9. 2015.

Szegedy, Christian, Vincent Vanhoucke, Sergey Ioffe, Jon Shlens, and Zbigniew Wojna. "Rethinking the inception architecture for computer vision." In Proceedings of the IEEE Conference on Computer Vision and Pattern Recognition, pp. 2818-2826. 2016.

He, Kaiming, Xiangyu Zhang, Shaoqing Ren, and Jian Sun. "Deep residual learning for image recognition." In Proceedings of the IEEE conference on computer vision and pattern recognition, pp. 770-778. 2016.

Simonyan, Karen, and Andrew Zisserman. "Very deep convolutional networks for large-scale image recognition." arXiv preprint arXiv: 1409.1556 (2014).

Krizhevsky, Alex, Ilya Sutskever, and Geoffrey E. Hinton. "ImageNet Classification with Deep Convolutional Neural Networks." Advances in neural information processing systems. 2012.

Huang, Gao, Zhuang Liu, Laurens Van Der Maaten, and Kilian Q. Weinberger. "Densely Connected Convolutional Networks." In CVPR, vol. 1, no. 2, p. 3. 2017.

Ekin D. Cubuk, Barret Zoph, Jonathon Shlens, Quoc V. Le. "RandAugment: Practical automated data augmentation with a reduced search space." arXiv: 1909.13719 (2019).

Ramprasaath R. Selvaraju, Michael Cogswell, Abhishek Das, Ramakrishna Vedantam, Devi Parikh, Dhruv Batra. "Grad-CAM: Visual Explanations from Deep Networks via Gradient-based Localization". (2016) arXiv: 1610.02391v4

Aditya Chattopadhyay, Anirban Sarkar, Prantik Howlader, Vineeth N Balasubramanian. "Grad-CAM++: Improved Visual Explanations for Deep Convolutional Networks". (2017) arXiv: 1710.11063

All documents mentioned in this specification are incorporated herein by reference in their entirety.

The terms "computer system" includes the hardware, software and data storage devices for embodying a system or carrying out a method according to the above described embodiments. For example, a computer system may comprise a central processing unit (CPU), input means, output means and data storage, which may be embodied as one or more connected computing devices. Preferably the computer system has a display or comprises a computing device that has a display to provide a visual output display (for example in the design of the business process). The data storage may comprise RAM, disk drives or other computer readable media. The computer system may include a plurality of computing devices connected by a network and able to communicate with each other over that network.

The methods of the above embodiments may be provided as computer programs or as computer program products or computer readable media carrying a computer program which is arranged, when run on a computer, to perform the method(s) described above.

The term "computer readable media" includes, without limitation, any non-transitory medium or media which can be read and accessed directly by a computer or computer system. The media can include, but are not limited to, magnetic storage media such as floppy discs, hard disc storage media and magnetic tape; optical storage media such as optical discs or CD-ROMs; electrical storage media such as memory, including RAM, ROM and flash memory; and hybrids and combinations of the above such as magnetic/optical storage media.

Unless context dictates otherwise, the descriptions and definitions of the features set out above are not limited to any particular aspect or embodiment of the invention and apply equally to all aspects and embodiments which are described.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

Other aspects and embodiments of the invention provide the aspects and embodiments described above with the term "comprising" replaced by the term "consisting of" or "consisting essentially of", unless the context dictates otherwise.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

The invention claimed is:

1. A computer implemented method for detecting foam on the surface of a liquid medium contained in a vessel of a bioreactor, the method including the steps of:

receiving a sample image of at least a portion of the vessel comprising the liquid-gas interface;

classifying the sample image between a first class and at least one second class, the first class and at least one second class being associated with different amounts of foam on the surface of the liquid, wherein the classifying is performed by a deep neural network classifier that has been trained using a plurality of training images of at least a portion of a vessel comprising a liquid-gas interface, wherein the plurality of training images comprise at least some images that differ from each other by one or more of: the location of the liquid-gas interface on the image, the polar and/or azimuthal angle at which the liquid-gas interface is viewed on the image, and the light intensity or colour temperature of the one or more light sources that illuminated the imaged portion of the vessel when the image was acquired; and responsive to classifying the sample image in the at least one second class, sending a signal to an effector device or a warning message to a user interface, wherein the effector is an antifoam agent dispensing system, an agitator system, an aeration system, a foam removal system, or a foam destruction system.

2. The method of claim 1, wherein the sample image and/or the training images is/are: side view(s) of the vessel, top view(s) of the vessel, and/or images acquired from outside the vessel.

3. The method of claim 2, wherein the sample image is an image acquired from outside the vessel.

4. The method of claim 1, wherein the first class is associated with the absence of foam on the surface of the liquid and the one or more second classes is/are associated with the presence of foam on the surface of the liquid, optionally wherein the absence of foam refers to the absence of clusters of bubbles on the surface of the liquid.

5. The method of claim 4, wherein the absence of foam refers to the absence of clusters of bubbles on the surface of the liquid, or wherein the absence of foam refers to the absence of a plurality of bubbles that together form a Voronoi tessellation pattern.

6. The method of claim 1, wherein the one or more second classes comprise a plurality of classes, wherein the plurality of classes are associated with the presence of different amounts of foam on the surface of the liquid.

7. The method of claim 1, wherein the plurality of training images comprise at least some images that differ from each other by the light intensity or colour temperature of the one or more light sources that illuminated the imaged portion of the vessel when the image was acquired, wherein said images were acquired using a plurality of light sources that differ in one or more of their power, colour temperature and brightness.

8. The method of claim 1, wherein the deep neural network is a convolutional neural network (CNN), optionally wherein the CNN is a CNN that has been pre-trained for object detection prior to training for foam detection using the training images.

9. The method of claim 1, wherein receiving a sample image of at least a portion of the vessel comprising the liquid-gas interface comprises acquiring an image of at least a portion of the vessel comprising the liquid-gas interface, and/or wherein the method further comprise selecting an area of a received sample image comprising the liquid-gas interface, optionally wherein selecting an area of a received sample image comprises applying a predefined mask to select an area of the received sample image.

10. The method of claim 1, wherein the sample image is a digital image acquired using image capture means that has distortion features similar to the distortion features in at least some of the plurality of training images, and/or wherein the sample image and the training images are each individually chosen from a colour image and a grayscale image, and/or wherein the plurality of training images comprise images obtained from other training images by image augmentation.

11. A method comprising:

performing a computer-implemented method for providing a tool for detecting foam on the surface of a liquid medium contained in a vessel of a bioreactor, the method comprising:

receiving:

a plurality of training images of at least a portion of a vessel of a bioreactor comprising a liquid-gas interface, wherein the plurality of training images comprise at least some images that differ from each other by one or more of: the location of the liquid-gas interface on the image, the polar and/or azimuthal angle at which the liquid-gas interface is viewed on the image, and the light intensity or colour temperature of the one or more light sources that illuminated the imaged portion of the vessel when the image was acquired; and a plurality of class labels, each associated with one of the plurality of training images, wherein the class labels are selected from a first class label and at least one second class label, and associated with different amounts of foam on the surface of the liquid; and training a deep neural network classifier to classify images between a first class and at least a second class using the plurality of training images;

defining a signal to be sent to an effector or user interface in response to an image of at least a portion of a vessel of a bioreactor comprising a liquid-gas interface being classified by the deep neural network classifier in the second class; and performing the computer implemented method for detecting foam on the surface of a liquid medium contained in a vessel of a bioreactor according to claim 1.

12. The method of claim 11, wherein:

(i) receiving a plurality of class labels, each associated with one of the plurality of training images, comprises displaying a plurality of training images and prompting a user to associate a class label with each of the plurality of training images; and/or (ii) the method further comprises selecting an area or a plurality of areas of each training image comprising the liquid-gas interface optionally by applying a user-defined or automatically defined mask to select an area of the received sample image; and/or (iii) the method further comprises defining a first signal to be sent to an effector device (and/or a user interface) when a sample image is classified in the second class or a first one of a plurality of second and further classes by the deep neural network classifier; and/or (iv) receiving a plurality of training images comprises acquiring a plurality of images, obtaining a plurality of images from a memory, or a combination thereof, optionally wherein acquiring a plurality of images of at least a portion of a vessel comprises modifying one or more of the following parameters at least once during the image acquisition process: the volume of liquid in the vessel, the position of the image acquisition means relative to the vessel, and the light intensity or colour temperature of the one or more light sources that illuminate the imaged portion of the vessel.

13. The method of claim 1, wherein the plurality of training images comprise:

at least some images that differ from each other by the location of the liquid-gas interface on the image, at least some images that differ from each other by the polar and/or azimuthal angle at which the liquid-gas interface is viewed on the image, and at least some images that differ from each other by the light intensity or colour temperature of the one or more light sources that illuminated the imaged portion of the vessel when the image was acquired.

14. The method of claim 1, wherein the first class is associated with the absence of foam on the surface of the liquid, and the one or more second classes comprise a plurality of classes, wherein the plurality of classes are associated with the presence of different amounts of foam on the surface of the liquid.

15. The method of claim 1, wherein the method further comprises selecting an area of a received sample image comprising the liquid-gas interface by applying a pre-defined mask to select an area of the received sample image.

16. A computer-implemented method for controlling a bioprocess in a vessel, the method comprising:

receiving a sample image of at least a portion of the vessel comprising the liquid-gas interface;

classifying the sample image between a first class and at least one second class, the first class and at least one second class being associated with different amounts of foam on the surface of the liquid, wherein the classifying is performed by a deep neural network classifier that has been trained using a plurality of training images of at least a portion of a vessel comprising a liquid-gas interface, wherein the plurality of training images comprise at least some images that differ from each other by one or more of:

the location of the liquid-gas interface on the image, the polar and/or azimuthal angle at which the liquid-gas interface is viewed on the image, and the light intensity or colour temperature of the one or more light sources that illuminated the imaged portion of the vessel when the image was acquired; and sending a first signal to an effector device if the sample image is classified in the second class or a first one of a plurality of second and further classes, wherein the effector device is selected from an antifoam agent dispensing system, an agitator system, an aeration system, a foam removal system and a foam destruction system; and repeating the steps of receiving a sample image, classifying the sample image and sending a signal to an effector device if the sample image is classified in the second class or a first one of a plurality of second and further classes, after a predetermined period of time has elapsed since receiving the preceding image.

17. The method of claim 16, wherein the vessel is a bioreactor.

18. The method of claim 16, wherein sending a first signal to an effector device comprises one or more of:

(i) sending a signal to an antifoam agent dispensing system to cause the antifoam agent dispensing system to dispense antifoam agent in the vessel, or to cause the antifoam agent dispensing system to increase the frequency and/or amount of antifoam agent dispensed in the vessel;

(ii) sending a signal to an agitator system coupled to the vessel to cause the agitator system to decrease the agitation speed in the vessel;

(iii) sending a signal to an aeration system coupled to the vessel to cause the aeration system to reduce the aeration rate in the vessel;

(iv) sending a signal to a foam removal system coupled to the vessel to cause the foam removal system to remove the foam in the vessel; and (v) sending a signal to a foam destruction system coupled to the vessel to cause the foam destruction system to generate vibrations suitable to destabilise foam in the vessel.

19. A system for detecting foam on the surface of a liquid medium contained in a vessel of a bioreactor, the system including:

at least one processor; and at least one non-transitory computer readable medium containing instructions that, when executed by the at least one processor, cause the at least one processor to perform operations comprising:

receiving a sample image of at least a portion of the vessel comprising the liquid-gas interface;

classifying the sample image between a first class and at least one second class, the first class and at least one second class being associated with different amounts of foam on the surface of the liquid, wherein the classifying is performed by a deep neural network classifier that has been trained using a plurality of training images of at least a portion of a vessel comprising a liquid-gas interface, wherein the plurality of training images comprise at least some images that differ from each other by one or more of:

the location of the liquid-gas interface on the image, the polar and/or azimuthal angle at which the liquid-gas interface is viewed on the image, and the light intensity or colour temperature of the one or more light sources that illuminated the imaged portion of the vessel when the image was acquired; and responsive to classifying the sample image in the at least one second class, sending a signal to an effector device or a warning message to a user interface, wherein the effector is an antifoam agent dispensing system, an agitator system, an aeration system, a foam removal system, or a foam destruction system.

20. One or more non-transitory computer readable media comprising instructions that, when executed by at least one processor, cause the at least one processor to perform a method for detecting foam on the surface of a liquid medium contained in a vessel of a bioreactor, the method including the steps of:

receiving a sample image of at least a portion of the vessel comprising the liquid-gas interface;

classifying the sample image between a first class and at least one second class, the first class and at least one second class being associated with different amounts of foam on the surface of the liquid, wherein the classifying is performed by a deep neural network classifier that has been trained using a plurality of training images of at least a portion of a vessel comprising a liquid-gas interface, wherein the plurality of training images comprise at least some images that differ from each other by one or more of: the location of the liquid-gas interface on the image, the polar and/or azimuthal angle at which the liquid-gas interface is viewed on the image, and the light intensity or colour temperature of the one or more light sources that illuminated the imaged portion of the vessel when the image was acquired; and responsive to classifying the sample image in the at least one second class, sending a signal to an effector device or a warning message to a user interface, wherein the effector is an antifoam agent dispensing system, an agitator system, an aeration system, a foam removal system, or a foam destruction system.

* * * * *